(12) United States Patent
Sharma

(10) Patent No.: US 11,793,957 B2
(45) Date of Patent: Oct. 24, 2023

(54) APPARATUS AND METHOD FOR MANIPULATING CHARACTERISTICS OF INHALED AIR

(71) Applicant: Vasu Sharma, Hyattsville, MD (US)

(72) Inventor: Vasu Sharma, Hyattsville, MD (US)

(*) Notice: Subject to any disclaimer, the term of this patent is extended or adjusted under 35 U.S.C. 154(b) by 296 days.

(21) Appl. No.: 16/995,131

(22) Filed: Aug. 17, 2020

(65) Prior Publication Data
US 2021/0052836 A1 Feb. 25, 2021

Related U.S. Application Data

(60) Provisional application No. 62/889,522, filed on Aug. 20, 2019.

(51) Int. Cl.
*A61M 15/00* (2006.01)
*A61M 15/08* (2006.01)
*A61M 16/16* (2006.01)

(52) U.S. Cl.
CPC .......... *A61M 15/08* (2013.01); *A61M 15/002* (2014.02); *A61M 16/161* (2014.02); *A61M 2205/3368* (2013.01)

(58) Field of Classification Search
CPC .... A61M 15/00; A61M 15/002; A61M 15/08; A61M 15/052; A61M 16/16; A61M 16/161; A61M 2205/0216; A61M 2205/3368; A61M 2205/3606; A61M 2205/3646; A61M 2205/502; A61M 2202/062; A61M 11/00; A61M 11/04; A61M 16/1045; A61M 16/105; A61M 16/1065; A61M 16/107; A63B 23/06

USPC .................................................... 128/203.22
See application file for complete search history.

(56) References Cited

U.S. PATENT DOCUMENTS

| 2,427,721 | A | 8/1946 | Goldstein |
| 2006/0085027 | A1 | 4/2006 | Santin et al. |
| 2008/0187609 | A1 | 8/2008 | Vail et al. |
| 2010/0108071 | A1* | 5/2010 | Macy, Jr. ............ A61M 16/107 128/205.27 |

(Continued)

FOREIGN PATENT DOCUMENTS

| DE | 202013010193 | 12/2013 |
| GB | 138079 | 7/1920 |

(Continued)

OTHER PUBLICATIONS

Patentability Search dated Jun. 29, 2020—18 Pages.

(Continued)

*Primary Examiner* — Justine R Yu
*Assistant Examiner* — Matthew R Moon
(74) *Attorney, Agent, or Firm* — McCarter & English, LLP

(57) ABSTRACT

Exemplary embodiments are directed to an apparatus for manipulating one or more characteristics of air to be inhaled. The apparatus includes an outer housing including an outer surface, a hollow interior, and at least one opening formed in the outer housing and extending between the outer surface and the hollow interior. The apparatus includes a manipulation enclosure disposed within the hollow interior of the outer housing, the manipulation enclosure capable of receiving therein an air characteristic manipulation component. A substantially continuous channel is formed between the manipulation enclosure and the outer housing.

18 Claims, 12 Drawing Sheets

(56) References Cited

U.S. PATENT DOCUMENTS

2014/0209096 A1 7/2014 Cheyene
2014/0305431 A1* 10/2014 Holley ............... A61M 16/161
                                                                128/205.24
2020/0288780 A1* 9/2020 Martin ................... A24F 40/20

FOREIGN PATENT DOCUMENTS

GB      2479586     10/2011
WO    2017089912    6/2017

OTHER PUBLICATIONS

International Search Report relating to PCT International Application No. PCT/US2020/046654, dated Nov. 20, 2020—8 pages.
Written Opinion relating to PCT International Application No. PCT/US2020/046654, dated Nov. 20, 2020—7 pages.

* cited by examiner

APPARATUS AND METHOD FOR MANIPULATING CHARACTERISTICS OF INHALED AIR

CROSS-REFERENCE TO RELATED APPLICATIONS

This application claims the benefit of U.S. Provisional Patent Application No. 62/889,522, which was filed on Aug. 20, 2019. The entire content of the foregoing provisional patent application is incorporated herein by reference.

TECHNICAL FIELD

The present disclosure relates to an apparatus for manipulating characteristics of inhaled air and, in particular, to a portable apparatus capable of controlling the temperature and/or humidity of air inhaled by the user.

BACKGROUND

A variety of devices exist in the industry for maintaining the comfort of an individual during hot temperatures. Such devices include, for example, cooling jackets, cooling watches, a robotic air conditioning unit that follows the user, or the like. For certain medical conditions, such as hot flashes, maintaining a cool environment can be helpful in reducing the discomfort of the user. However, traditional devices generally do not allow for manipulation of air to be inhaled by the user.

Thus, a need exists for a portable apparatus that allows a user to manipulate or change the characteristics of air directly inhaled by the user. These and other needs are addressed by the apparatus and method of the present disclosure.

SUMMARY

In accordance with embodiments of the present disclosure, an exemplary apparatus for manipulating one or more characteristics of air to be inhaled is provided. The apparatus includes an outer housing including an outer surface, a hollow interior, and at least one opening formed in the outer housing and extending between the outer surface and the hollow interior. The apparatus includes a manipulation enclosure disposed within the hollow interior of the outer housing, the manipulation enclosure capable of receiving therein an air characteristic manipulation component. A substantially continuous channel is formed between the manipulation enclosure and the outer housing.

In some embodiments, the outer housing can define a substantially rectangular, cylindrical, or spherical configuration. The outer housing includes inner surfaces and one or more support structures extending inwardly into the hollow interior from one or more of the inner surfaces. In some embodiments, the support structures can extend inwardly from each inner surface of the outer housing. In some embodiments, rather than the outer housing, the manipulation enclosure can include one or more support structures extending outwardly into the hollow interior of the outer housing from outer surfaces of the manipulation enclosure. In some embodiments, the outer housing can enclose all surfaces of the manipulation enclosure. In some embodiments, the apparatus can include a cover detachable from the outer housing for enclosing the manipulation enclosure within the outer housing. In such embodiments, the substantially continuous channel can also be formed between the manipulation enclosure and the cover.

In some embodiments, the cover can include one or more support structures extending inwardly into the hollow interior of the outer housing from an inner surface of the cover. In some embodiments, the manipulation cover can include one or more support structures extending outwardly into the hollow interior of the outer housing. The one or more support structures of the outer housing and the cover can abut outer surfaces of the manipulation enclosure to form the substantially continuous channel around the manipulation enclosure. The substantially continuous channel can extend entirely around outer surfaces of the manipulation enclosure. The substantially continuous channel can extend entirely around each side of the manipulation enclosure.

In some embodiments, a width or hydraulic diameter of the substantially continuous channel can be less than or equal to about 1.0 mm. In some embodiments, a width or hydraulic diameter of the substantially continuous channel can be about 1.0 mm to about 10 mm. In some embodiments, the width or hydraulic diameter of the substantially continuously channel can be substantially uniform around each outer surface of the manipulation enclosure.

In some embodiments, a front surface of the outer housing can include a recessed groove configured and dimensioned to at least partially received the cover therein. The cover includes at least one extension protruding from one surface of the cover (or from the apparatus if the apparatus does not include a cover), and at least one hole extending through the cover to fluidly connect the at least one extension with the substantially continuous channel. In such embodiments, the at least one extension can be configured to be at least partially inserted into a nostril of a user. In some embodiments, the apparatus can include a single, wider extension protruding from one end of the apparatus, the extension including an opening fluidly connected to the substantially continuous channel, and the opening configured to be placed at least partially around a bottom surface of a nose of a user to cover at least one nostril of the user with the extension. In some embodiments, the extension can also act as a cover for the apparatus. The outer housing can be configured to receive air through the at least one opening and into the substantially continuous channel, and the air characteristic manipulation component disposed within the manipulation enclosure is configured to modify at least one of a temperature or a humidity of the air prior to inhalation of modified air by a user.

In some embodiments, the outer housing can be fabricated from a flexible material that allows the outer housing to at least partially conform to a contoured area of a user's face. In some embodiments, the air characteristic manipulation component can be at least one of a thermal storage material, a phase change material, a desiccant, or water. In some embodiments, the manipulation enclosure can include one or more passages formed therein, each of the one or more passages configured to allow air passage therethrough. In some embodiments, the apparatus can include a feedback loop including one or more sensors configured to detect an ambient air temperature and a modified air temperature. In such embodiments, the apparatus can include a processing device configured to control manipulation of one or more characteristics of ambient air based on input from the one or more sensors of the ambient air temperature and the modified air temperature.

In accordance with embodiments of the present disclosure, an exemplary apparatus for manipulating air to be inhaled is provided. The apparatus includes an outer housing including an outer surface, a hollow interior, and at least one opening formed in the outer housing and extending between the outer surface and the hollow interior. The apparatus includes a manipulation enclosure disposed within the hollow interior of the outer housing, the manipulation enclosure including an air characteristic manipulation component disposed therein. The apparatus includes a cover attached to the outer housing, the cover enclosing the manipulation enclosure within the hollow interior of the outer housing. A substantially continuous channel is formed between the manipulation enclosure and the outer housing, and between the manipulation enclosure and the cover. The outer housing is configured to receive air through the at least one opening and into the substantially continuous channel, and the air characteristic manipulation component is configured to modify at least one of a temperature or a humidity of the air prior to inhalation of modified air by a user. The substantially continuous channel extends entirely around each outer surface of the manipulation enclosure.

In accordance with embodiments of the present disclosure, an exemplary method of manipulating air to be inhaled is provided. The method includes introducing air into an outer housing of an apparatus through at least one opening formed in the outer housing and extending between an outer surface of the outer housing and a hollow interior of the outer housing. The apparatus includes a manipulation enclosure disposed within the hollow interior of the outer housing, the manipulation enclosure capable of receiving therein an air characteristic manipulation component. A substantially continuous channel is formed between the manipulation enclosure and the outer housing. The method includes passing the air around at least a portion of the manipulation enclosure to modify at least one characteristic of the air. The method includes passing modified air out of the apparatus for inhalation by a user.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

To assist those of skill in the art in making and using the disclosed apparatus and method, reference is made to the accompanying figures, wherein.

DESCRIPTION OF EXEMPLARY EMBODIMENTS

Figure 1:
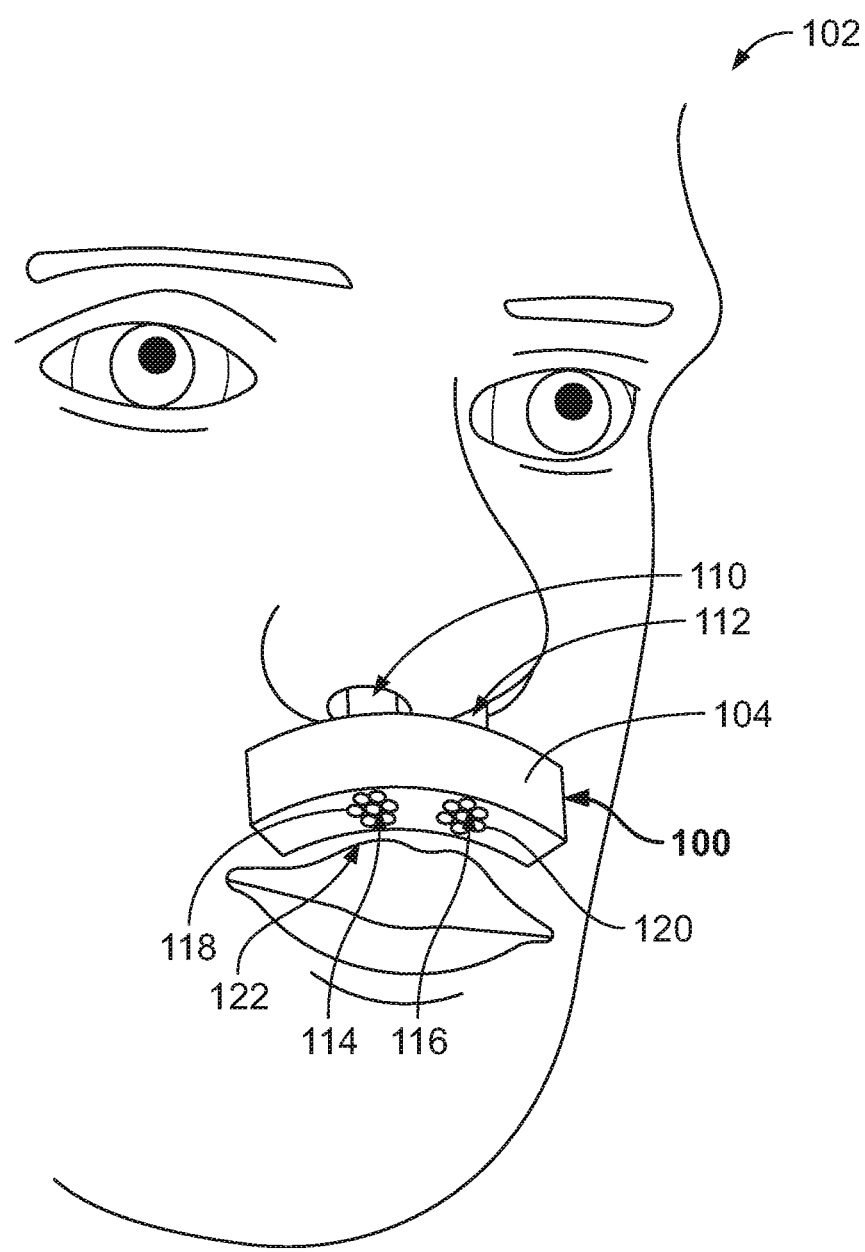
FIG. 1 is a perspective view of an exemplary apparatus for manipulating characteristics of inhaled air according to the present disclosure in use by a user.

In accordance with embodiments of the present disclosure, an exemplary apparatus for manipulating characteristics of inhaled air is provided. The apparatus generally includes an assembly of an outer housing, and a manipulation enclosure disposed within the outer housing and capable of receiving therein an air characteristic manipulation component. In some embodiments, the outer housing can fully enclose the manipulation enclosure. In some embodiments, the apparatus can include a cover capable of being coupled, engaged or interlocked with the housing to enclose the manipulation enclosure within the outer housing. The manipulation enclosure fits within the outer housing and the outer housing includes inner features or protrusions that space the manipulation enclosure away from the inner walls to define a substantially continuous air gap or channel between the manipulation enclosure and the outer housing. The air gap or channel allows for flow of air around the manipulation enclosure, thereby adjusting the temperature and/or humidity of the air prior to inhalation by the user. The air gap or channel in combination with the air characteristic manipulation component within the manipulation enclosure form a heat exchanger within the apparatus for manipulating one or more characteristics of the air prior to inhalation by the user.

By manipulating or changing the characteristics of air prior to inhalation by the user, the exemplary apparatus can provide thermal comfort to the user. The exemplary apparatus can also manipulate or change the characteristics of air prior to inhalation to alleviate discomfort for certain medical conditions, such as hot flashes, multiple sclerosis, cardiac arrest, or the like. For example, the apparatus is capable of quickly cooling the air to be inhaled by the user to provide targeted cooling of the brain or prioritizing cooling of the brain and the user. As a further example, respiratory cooling provided by the apparatus can prioritize cooling of the brain of the patient to provide quick comfort to the user. Although discussed herein as manipulating or changing temperature and/or humidity, it should be understood that the exemplary apparatus can manipulate or change a variety of one or more characteristics of the air, e.g., temperature, humidity, odor/smell, or the like. In some embodiments, in addition to manipulating the temperature and/or humidity of the inhaled air, the apparatus can manipulate the odor and/or smell of the inhaled air. In some embodiments, the apparatus can manipulate the odor and/or smell of the inhaled air separately from the temperature and/or humidity manipulation. The apparatus can operate both indoors and outdoors to provide thermal comfort to the user. In some embodiments, the apparatus can be used to facilitate cooling for firefighters, athletes, or those in a thermal rehabilitation process. In some embodiments, the apparatus can be used as a replacement for traditional air conditioning systems, providing a solution having increased energy efficiency technology.

In some embodiments, the apparatus can be inserted or plugged into one or both nostrils during use. When inserted into both nostrils, the majority of the air manipulated by the apparatus can be inhaled by the user. In some embodiments, even with the apparatus inserted into both nostrils, the apparatus can provide a fraction of the air needed for inhalation (e.g., about 90%, about 85%, or the like), with the remaining air inhaled by the user coming from outside of the apparatus. When inserted into only a single nostril, only a partial amount of manipulated air by the apparatus is inhaled by the user. In some embodiments, the manipulation enclosure can receive therein an air characteristic manipulation component (e.g., a phase change material (PCM)), and the apparatus can use latent and/or sensible heat of the phase change material to manipulate the characteristics of breathed air. The term "phase change material" can refer to any material that utilizes latent heat of fusion and/or vaporization for storage of thermal energy. In some embodiments, the manipulation enclosure can receive therein an air characteristic manipulation component (e.g., a thermal storage material (TSM)), and the apparatus can use latent and/or sensible heat of the thermal storage material to manipulate the characteristics of breathed air. In some embodiments, a desiccant material (e.g., a hygroscopic material) can be used to manipulate the characteristics of breathed air, such as temperature and/or humidity. In some embodiments, the manipulation enclosure can include a combination of a phase change material, a thermal storage material, and/or a desiccant material. In some embodiments, the manipulation enclosure can include both a desiccant material, and a thermal storage material or a phase change material to manipulate the characteristics of breathed air in combination. In some embodiments, the apparatus only includes a single air characteristic manipulation component in the form of a phase change material, a thermal storage material, or a desiccant material. It should be understood that the material of the air characteristic manipulation component can be any type of material that can be used as a thermal energy source and/or heat sink. In some embodiments, any phase change material with a melting temperature of less than or equal to about 20° C. can be used. In some embodiments, water ($H_2O$) can be used as a thermal storage material or a phase change material. Using water can provide an advantage of having very high latent heat of fusion (one of the highest) and a low melting point. Using water (as well as the other air characteristic manipulation components) provides a material that is safe to use on or near the eyes, skin and/or nostrils of the user. Water also provides a low material cost for operation of the apparatus.

The manipulation enclosure for receiving the air characteristic manipulation component can define a variety of different shapes and/or sizes (e.g., hollow sphere, arc of a hollow ring, ring, cube, cuboid, hollow cylinder, combination of arcs of hollow rings, or the like). The configuration of the manipulation enclosure can be selected to substantially match the topology of the features of the face, head, chin, neck, or the like, for proper positioning of the apparatus. In some embodiments, the outer housing of the apparatus can be formed from a partially flexible material (e.g., silicon rubber, or the like) to allow the apparatus to at least partially conform to the features of the face on which the apparatus is to be positioned. The overall shape of the manipulation enclosure can be selected to substantially match the configuration or shape of the outer housing to accommodate the manipulation enclosure within the outer housing in a spaced matter (e.g., to form the gap between the manipulation enclosure and the inner walls of the outer housing). The manipulation enclosure can include a hollow interior such that thermal storage material and/or phase change material can be filled into the hollow interior for operation of the heat exchanger In some embodiments, the material used for fabrication of one or more components of the apparatus can be food grade material.

The apparatus can be configured and dimensioned to be positioned in a space defined by or surrounding the nose, upper lip, lower lip and cheeks of the user. In some embodiments, the apparatus can be configured and dimensioned to be positioned above the upper lip and below the nose of the user, with one or two inhalation projections at the top of the apparatus configured to be inserted into one or both nostrils, respectively, of the user. In some embodiments, the apparatus can be configured and dimensioned to be positioned at least partially within the mouth or oral cavity of the user. In some embodiments, the apparatus can include one or more circular or non-circular tubes, channels or gaps that allow for air flow to facilitate thermal energy flow and/or material flow (when desiccant is used) between the air and the thermal storage material, phase change material, and/or desiccant material. Similar to nostril applications, when positioned at least partially within the mouth or oral cavity, the apparatus can supply substantially all or only part of the air to be inhaled by the user. In some embodiments, the apparatus can in combination connect to one or more nostrils of the user, and the mouth and/or oral cavity of the user.

In some embodiments, the miniature heat exchanger within the apparatus can include a substantially continuous gap between the outer housing and cover of the apparatus, and the manipulation enclosure. In some embodiments, the miniature heat exchanger within the apparatus for transferring thermal energy can include one or more circular or non-circular tubes, channels and/or gaps at least partially extending within the apparatus. In such embodiment, the heat exchanger aids in facilitating thermal energy flow and/or material flow between the air and the thermal storage material, phase change material, and/or the desiccant material. The miniature heat exchanger formed by the apparatus can be used to transfer heat between the air characteristic manipulation component within the manipulation enclosure and the air within the apparatus prior to inhalation of the air by the user. As used herein, the term "miniature heat exchanger" can refer to a micro-channel heat exchanger having tubes and/or channels with a hydraulic diameter (or gap with a width) of about, e.g., less than or equal to 1 mm, 1-10 mm, 1-9 mm, 1-8 mm, 1-7 mm, 1-6 mm, 1-5 mm, 1-4 mm, 1-3 mm, 1-2 mm, 2-8 mm, 3-7 mm, 4-6 mm, 2-10 mm, 3-10 mm, 4-10 mm, 5-10 mm, 6-10 mm, 7-10 mm, 8-10 mm, 9-10 mm, 1 mm, 2 mm, 3 mm, 4 mm, 5 mm, 6 mm, 7 mm, 8 mm, 9 mm, 10 mm, or the like.

In some embodiments, the apparatus can manipulate or change characteristics of the complete volume of inhaled air (e.g., the entire volume of air inhaled into the apparatus and further inhaled by the user). In some embodiments, the apparatus can manipulate or change characteristics of a fraction of the total inhaled air. For example, the apparatus can manipulate or change characteristics of about, e.g., 50-99%, 50-95%, 55-90%, 60-85%, 65-80%, 70-75%, 50%, 55%, 60%, 65%, 70%, 75%, 80%, 85%, 90%, 95%, or the like, of the total air inhaled into the apparatus.

In some embodiments, the user can control or customize the percentage of air to be manipulated by the apparatus. In some embodiments, the user can control or customize the characteristics or conditions of the air supplied to the user through the apparatus. For example, the apparatus can include a user interface through which the user can adjust the temperature and/or humidity level to be provided to the user through the apparatus after passage around the manipulation enclosure. In some embodiments, the apparatus can manipulate a predetermined percentage of air to be inhaled by the user through the apparatus, and the user does not have control of such percentage. The temperature and/or humidity of the air inhaled into the apparatus can be further manipulated by the nasal cavity to reach alveolar conditions. For example, upon inhalation of air from the apparatus, the body of the user can lose or gain heat depending on the characteristics of the air supplied to the user from the apparatus. In particular, after manipulation by the apparatus, the air inhaled by the user can create a sensation of thermal comfort (in addition to other possible potential effects) to the user. Such effect of thermal comfort can be generated by the phenomenon referred to as nasal cooling or respiratory cooling (conditioning air inhaled by nose). Nasal cooling or respiratory cooling describes a process in which the body of the user attempts to change the characteristics of the inhaled air to match the alveolar conditions (e.g., characteristics of air by lungs).

The air inhaled by the user enters the lungs for exchange of oxygen and/or other constituents of air. The one or more paths in the body connecting the external environment (e.g., outside air) and the lungs have special capabilities/functions of manipulating the characteristics of inhaled air to ensure that the inhaled air is safe for the user. In the process of manipulating the characteristics of inhaled air, the body can lose or gain heat depending on the characteristics of the supplied air. For example, if the supplied air is cold and has a low humidity, the body can increase the temperature of the air and add moisture to the air to ensure the air is safe for the user. As used herein, the term "supplied air" refers to the air entering the body of the user, which may or may not be manipulated by the apparatus (e.g., depending on the percentage of air the apparatus is configured to manipulate). As an example, if the apparatus is being used, the supplied air is the air supplied from the apparatus for inhalation. As a further example, if the apparatus is not being used, the supplied air is the air inhaled from around the user.

The apparatus can take advantage of the body's natural phenomenon/process of manipulating characteristics of the breathed air to match (or substantially match) the alveolar conditions. For example, the apparatus can reduce the temperature and/or humidity of ambient air entering the body through the apparatus. The cooled air from the apparatus therefore travels through the passage/pathway to the lungs, where the passage/pathway can try to increase the temperature and/or humidity of the cooled air to match the alveolar conditions. Alveolar conditions are generally (but not necessarily) about 36° C. and about 90% relative humidity. When the cooled air is heated and receiving moisture, the body loses thermal energy or heat and thereby, the body is cooled.

During experimentation with the exemplary apparatus, it was recognized that manipulating the characteristics of inhaled or breathed air can have a significant effect on the thermal comfort of the user, and can further provide various other benefits. Experimentation further validated the hypothesis formed on the basis of scientific facts. Integrating the air characteristic manipulation component with a micro-channel heat exchanger unit allows for technology to be developed that can significantly manipulate the characteristics of breathed air without being too heavy and/or cumbersome to the user.

In some embodiments, the apparatus can include one or more sensors (e.g., a sensing or feedback system), and can use the one or more sensors to measure/detect characteristics of ambient air, such as temperature and/or humidity. A feedback loop within the apparatus can be in communication with the sensors to control the characteristics of the manipulated air within the apparatus based on the detected characteristics of ambient air. For example, if the sensors detect a temperature and/or humidity beyond a predetermined threshold value considered to provide comfort to the user, the feedback loop can control operation of the apparatus to ensure the desired characteristics of the manipulated air are maintained, resulting in continued comfort of the user. In some embodiments, the feedback loop and operation can be automatic. In some embodiments, the feedback loop and operation can be (at least partially) manually controlled by the user.

In some embodiments, a heat exchanging fluid (e.g., the breathed or supplied air) can flow completely around the manipulation enclosure (e.g., the thermal storage material or phase change material reservoir) in the gap available around the manipulation enclosure. The gap between the outer housing of the apparatus and the manipulation enclosure advantageously minimizes the heat exchange between the manipulation enclosure and any surface, material or fluid of the apparatus that is not assisting in manipulating the characteristics of air inside of the apparatus. Such design of the heat exchanger provides an efficient and effective manipulation of the air, and can increase the overall operational time of the apparatus. In some embodiments, the manipulation enclosure can be removable from the outer housing to allow for recharging of the manipulation enclosure, e.g., by freezing, or the like.

Figure 2:
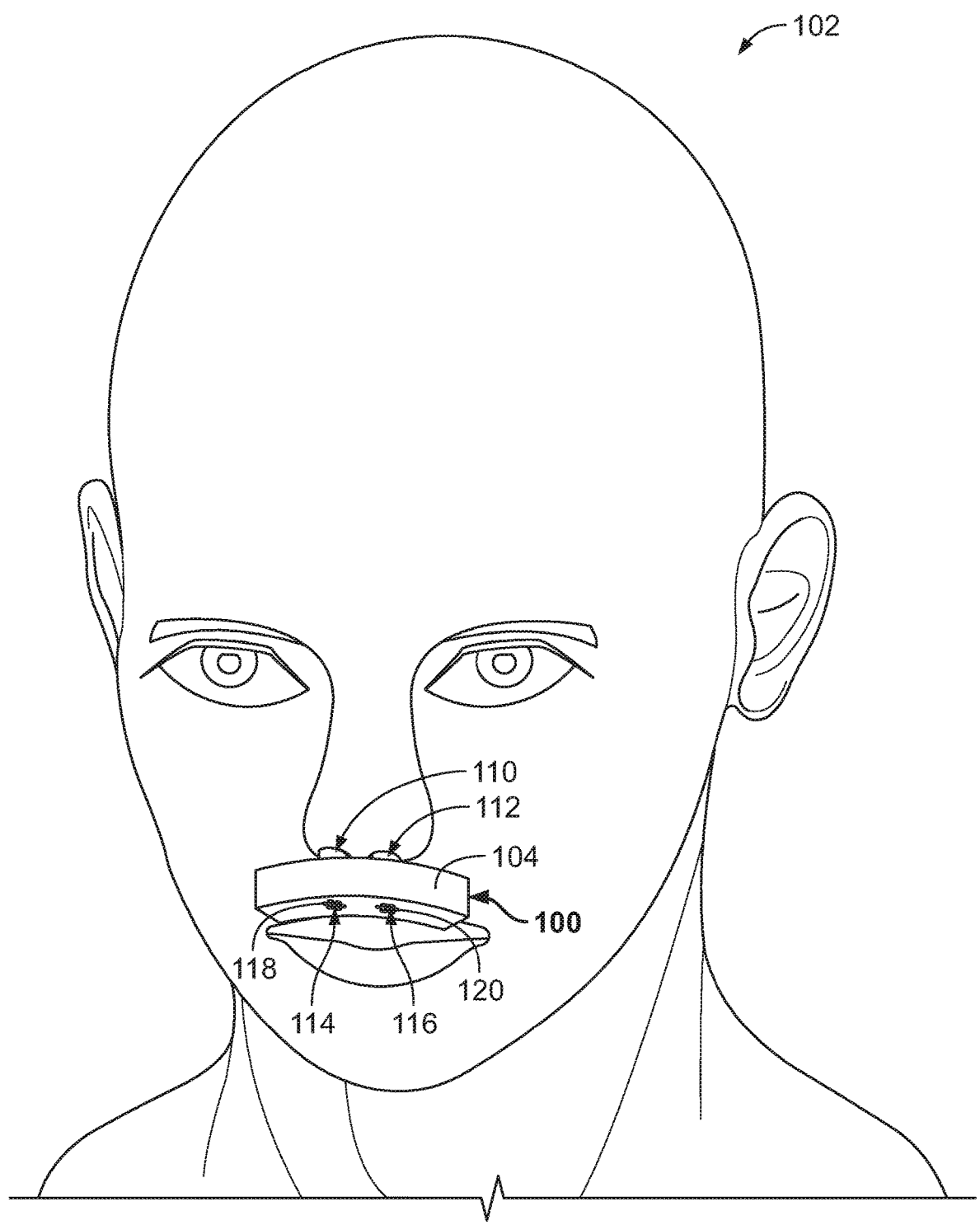
FIG. 2 is a perspective view of an exemplary apparatus for manipulating characteristics of inhaled air according to the present disclosure in use by a user.
Figure 3:
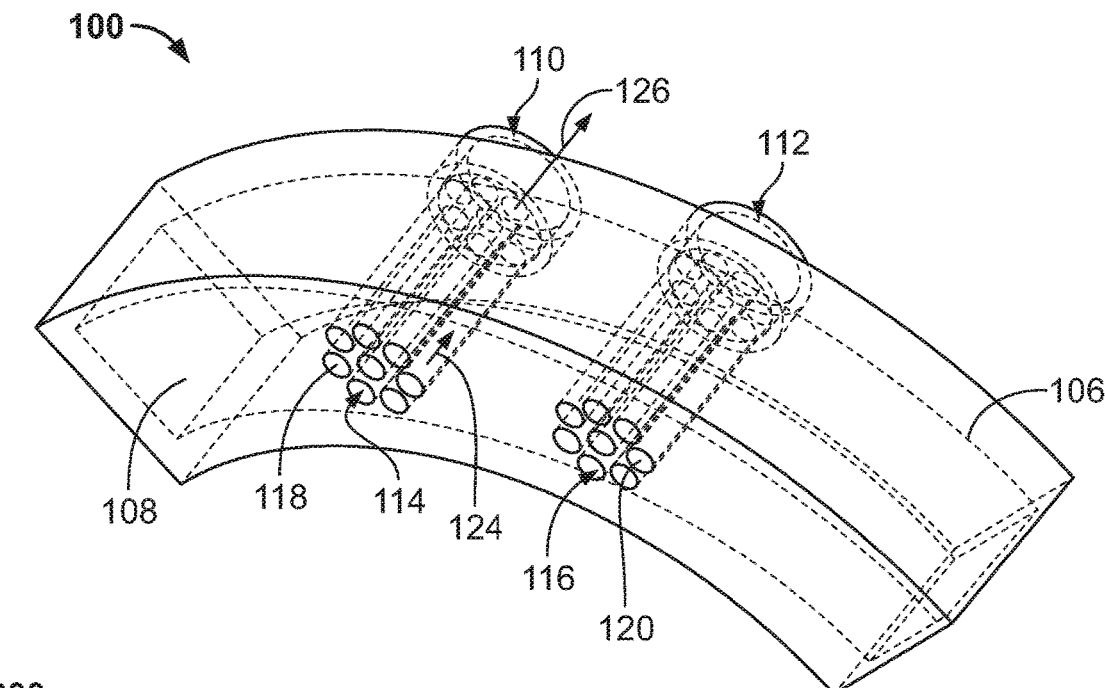
FIG. 3 is a perspective view of an exemplary apparatus for manipulating characteristics of inhaled air according to the present disclosure.

FIGS. 1-3 show perspective views of an exemplary apparatus 100 for manipulating or changing one or more characteristics of air to be inhaled by a user 102. The apparatus 100 includes a body or outer housing 104 configured and dimensioned to be positioned between the upper lip and nose of the user 102. In some embodiments, the apparatus 100 can be positioned in a different area of the user 102, e.g., the neck, face, head, or the like. The housing 104 includes a hollow interior capable of receiving a manipulation enclosure 106. The manipulation enclosure 106 can, in turn, receive therein an air characteristic manipulation component 108 (e.g., a phase change material, a thermal storage material, a desiccant, combinations thereof, or the like). For example, the manipulation enclosure 106 can include a substantially hollow interior capable of receiving the manipulation component 108. In some embodiments, the manipulation enclosure 106 can be configured such that the solid portion of the component 108 floats within the manipulation enclosure 106 above the melted portion of the component 108 to maintain the solid portion of the component 108 around the heat exchanger(s). Although illustrated as substantially rectangular in shape, it should be understood that the interior space for the manipulation enclosure 106 can be any shape and/or configuration. The manipulation enclosure 106 can be substantially complementary in shape to the interior of the housing 104.

In some embodiments, the interior of the housing 104 can define a rectangular, curved shape (e.g., a mustache shape). In some embodiments, the interior of the housing 104 can be, e.g., a hollow sphere, a hollow cube, a hollow cuboid, a hollow cylinder, a hollow ring, or any other similar geometry. In some embodiments, the interior and the exterior of the housing 104 can be configured to substantially match the contour of the body of the user 102 where the apparatus 100 is to be positioned. For example, the apparatus 100 and/or the interior of the housing 104 can be contoured to substantially match the cheeks, chin, nose and/or lips of the user 102. In some embodiments, the apparatus 100 and/or the interior of the housing 104 can be rigid in shape and may or may not match the contour of the location in which it is positioned on the user 102.

In some embodiments, the apparatus 100 and/or the housing 104 can be fabricated from a flexible material, e.g., a food grade silicon rubber, or the like. The flexible material allows the apparatus 100 to deform at least slightly to fit or accommodate the contour of the user 102. The overall shape of the apparatus 100 can thereby be customized to better fit each individual user 102. In some embodiments, deformation of the shape of the apparatus 100 can be a result of a gravitational force and/or a physical constraint of the location of the body of the user 102 on which the apparatus 100 is positioned.

The apparatus 100 includes one or more extensions 110, 112 extending from a top surface of the housing 104. The extensions 110, 112 can be configured and dimensioned to fit at least partially within the respective nostrils of the user 102 to maintain the apparatus 100 in the desired position on the face of the user 102. In some embodiments, the apparatus 100 can include an extension capable of being inserted into one nostril of the user 102. In some embodiments, the apparatus 100 can include two extensions capable of being inserted into respective nostrils of the user 102 (e.g., extensions 110, 112). In some embodiments, the apparatus 100 can include an extension capable of at least partially fitting and surrounding the outer surface of the nose of the user to provide modified air to at least one nostril of the user (see, e.g., FIG. 18).

In some embodiments, the extensions 110, 112 in combination with the upper lip, for example, can assist in maintaining the desired position of the apparatus 100 on the face of the user 102. The extensions 110, 112 can define a substantially cylindrical shape with a hollow interior or passage 114, 116. In some embodiments, the outer diameter of each extension 110, 112 can be about, e.g., 5-30 mm, 10-30 mm, 15-25 mm, 20-25 mm, 5 mm, 10 mm, 15 mm, 20 mm, 25 mm, 30 mm, or the like. Air manipulated by the apparatus 100 can pass through the passages 114, 116 and into the nasal airway of the user 102. In some embodiments, the extensions 110, 112 can maintain or assist in maintaining the position of the apparatus 100 relative to the user 102, and direct manipulated air to the nostrils of the user 102. In some embodiments, additional supports can be used to assist in maintaining the position of the apparatus 100 relative to the user 102. In some embodiments, the apparatus 100 can include one or more handles extending from the outer housing 104, with the handles capable of being grasped to maintain the desired position of the apparatus 100. In some embodiments, the apparatus 100 can be simply held in the hand of the user with the outer housing 104 and/or other structures of the apparatus 100 acting as a handle or structure capable of being grasped. In some embodiments, the apparatus 100 can include a wider extension structure with at least two openings formed therein for direction manipulated air into at least one nostril of the user 102 (see, e.g., FIG. 18). In such embodiment, the wider support structure can be positioned over the bottom portion of the nose of the user 102, substantially fitting or matching the exterior bottom contour of the nose, with a substantially tight seal formed between the support structure and the nose. The wider support structure can assist in maintaining the position of the apparatus 100 relative to the nose of the user 102.

In some embodiments, the apparatus 100 can include a single extension 110, 112, with the single extension 110, 112 plugged or inserted into only one of the nostrils of the user 102. In some embodiments, the apparatus 100 of FIGS. 1-3 can be used such that only one of the extensions 110, 112 is plugged or inserted into one of the nostrils of the user 102, with the other extensions 110, 112 moved sideways to avoid the second nostril of the user 102. The extensions 110, 112 can be fabricated from, e.g., a food grade rubber or silicon, a food grade plastic, any other food grade material, any other flexible material, any plastic, any polymer, or the like. The material of fabrication may provide flexibility to the extensions 110, 112 such that the extensions 110, 112 can at least partially conform to the inner walls of the nostrils of the user 102 for a better and substantially air tight fit. Although illustrated as cylindrical in shape, the extensions 110, 112 can be of any shape, e.g., bulbous, tapered, or the like. In some embodiments, the extensions 110, 112 can define a varying diameter or radius (e.g., an initially increasing radius up to a predetermined value in a direction away from the outer housing 104, and subsequently a gradually decreasing radius). In some embodiments, the extensions 110, 112 can include grooves and/or protrusions along the outer surface to enhance the grip of the extensions 110, 112 within the nostrils of the user 102, with such grooves and/or protrusions assisting in maintaining the position of the apparatus against the forces of gravity.

The apparatus 100 includes one or more heat exchangers 114, 116 formed within the housing 104. Although illustrated as two separated heat exchangers 114, 116 with each heat exchanger 114, 116 providing manipulated air to the respective extensions 110, 112, it should be understood that the apparatus 100 can include a single or combined heat exchanger 114, 116 directing manipulated air to both extensions 110, 112. Each heat exchanger 114, 116 can include one or more channels 118, 120 (e.g., tubes, gaps, or the like). The channels 118, 120 can extend from the bottom surface of the housing 104 to the top surface of the housing 104, and connect to the respective inner passages 114, 116 of the extensions 110, 112 at the top surface of the housing 104.

The cross-section of each of the channels 118, 120 can be circular or non-circular. In some embodiments, the channels 118, 120 can be formed by substantially circular or cylindrical tubes. In some embodiments, each of the channels 118, 120 can define an outer diameter of about 2.4 mm and an inner diameter of about 2 mm. In some embodiments, each of the channels 118, 120 can define an outer diameter of about, e.g., 0.2-10 mm, 0.2-5 mm, 0.2-3 mm, 0.2-1 mm, 2-3 mm, 2.1-2.9 mm, 2.2-2.8 mm, 2.3-2.7 mm, 2.4-2.6 mm, 0.2 mm, 0.3 mm, 0.4 mm, 0.5 mm, 1 mm, 2 mm, 2.1 mm, 2.2 mm, 2.3 mm, 2.4 mm, 2.5 mm, 2.6 mm, 2.7 mm, 2.8 mm, 2.9 mm, 3 mm, or the like. In some embodiments, each of the channels 118, 120 can define a hydraulic diameter of about, e.g., 0.1-3 mm, 0.1-2 mm, 0.1-1 mm, 0.5-2 mm, 0.5-1 mm, 1-2 mm, 1.1-1.9 mm, 1.2-1.8 mm, 1.3-1.7 mm, 1.4-1.6 mm, 1-1.5 mm, 1-1.4 mm, 1-1.3 mm, 1-1.2 mm, 1-1.1 mm, 1.5-2 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, less than or equal to 1 mm, or the like. The minimal hydraulic diameter of the channels 118, 120 forms a microchannel heat exchanger. As air passes through the channels 118, 120, the component 108 cools (or heats) the air, and optionally removes humidity from the air, before directing the air to the nostrils of the user 102. The configuration and size of the channels 118, 120 allows multiple passages to be used in a minimal space, and increases the overall heat exchange provided by the component 108.

As shown in FIGS. 1-3, each of the heat exchangers 114, 116 can include a group of two or more of the channels 118, 120. In some embodiments, each channel 118, 120 can define a uniform cross-section between the top and bottom surfaces of the housing 104. In some embodiments, each channel 118, 120 can change in cross-section between the top and bottom surfaces of the housing 104 (e.g., tapering outward, tapering inward, combinations thereof, or the like). In some embodiments, the outer surface of each of the channels 118, 120 can be fabricated from a thermal conducting material to improve the thermal energy transfer from the component 108 to the air passing through the channels 118, 120. For example, the channels 118, 120 can be formed from a cylindrical metal within a plastic housing such that the entire heat exchange surface, i.e., the surface between the air and the component 108, is thermally conducting. The channels 118, 120 are surrounded by the component 108, thereby improving thermal conducting and energy transfer between the component 108 and the air passing through the channels 118, 120. In some embodiments, the outer surface of each of the channels 118, 120 can be fabricated from a non-conducting material. In such embodiments, the proximity of the channels 118, 120 to the component 108 and/or the thin walls of the channels 118, 120 allows for thermal transfer without the use of a thermal conducting material.

In some embodiments, eight stainless steel tubes or channels 118, 120 with thin walls can be used for each of the heat exchangers 114, 116. In some embodiments, the wall thickness for each of the channels 118, 120 can be about, e.g., 0.01-2 mm, 0.01-1 mm, 0.01-0.5 mm, 0.01 mm, 0.1 mm, 0.5 mm, 1 mm, 2 mm, or the like. In some embodiments, the effective length of the channels 118, 120 (as measured between the top and bottom surfaces of the housing 104) can be chosen to prevent fully formed fluid flow of breathed air. In the entry region of the fluid flow at the bottom surface of the housing 104 (e.g., not fully developed fluid flow), the heat transfer coefficient can be greater than for fully developed flow. The overall length of the channels 118, 120 can be selected to maintain the non-fully developed fluid flow (e.g., turbulent) to improve energy transfer. In some embodiments, the length of each of the channels 118, 120 can be substantially equal. In some embodiments, the length of the channels 118, 120 can be different. For example, if "n" number of channels 118, 120 are used in each of the heat exchangers 114, 116, one or more channels 118, 120 can have a different length than all other "n–1" channels 118, 120. In some embodiments, the effective heat exchanging length of each channel 118, 120 can be adjustable, allowing for the apparatus 100 to be customized in terms of the amount of heat exchanged. For example, if "n" number of channels 118, 120 are used in each heat exchanger 114, 116, each channel 118, 120 can have a different amount of variation or change in length than all other "n–1" channels 118, 120.

In some embodiments, the total effective cross-sectional area of all of the channels 118, 120 (e.g., the sum of the cross-sectional areas of the channels 118, 120) can be equal to or greater than the effective breathing cross-sectional area of both nostrils and/or the mouth/oral cavity of the user 102. In some embodiments, the total effective cross-sectional area of the channels 118, 120 for the respective heat exchanger 114, 116 can be equal to or greater than the effective breathing cross-sectional area of the respective nostril of the user 102. In some embodiments, the total effective cross-sectional area of the channels 118, 120 can be equal to or greater than about, e.g., 30-100%, 30-90%, 30-80%, 30-70%, 30-60%, 30-50%, 30-40%, 40-100%, 50-100%, 50-90%, 50-80%, 50-70%, 50-60%, 60-100%, 70-100%, 80-100%, 90-100%, 30%, 40%, 50%, 60%, 70%, 80%, 90%, 100%, or the like, than the effective breathing cross-sectional area of both nostrils of the user 102.

For example the average effective diameter of decongested nasal passages can be estimated at about 3 mm. If the apparatus 100 is manipulating the complete quality of air entering one decongested nostril, the effective area of all channels 118, 120 used in the heat exchanger 114, 116 is greater than the area of a cylinder with an internal diameter of about 3 mm (e.g., the cylinder representing the nasal passage). In some embodiments, the apparatus 100 can be configured such that the average effective diameter of the decongested nasal passage is not assumed to be 3 mm, e.g., about 1-5 mm, 1-4 mm, 1-3 mm, 1-2 mm, 2-5 mm, 3-5 mm, 4-5 mm, 1 mm, 2 mm, 3 mm, 4 mm, 5 mm, or the like.

During use, the user 102 places the apparatus 100 in the appropriate position of the user's body (e.g., between the nose and upper lip), and inserts one or more of the extensions 110, 112 at least partially into the nostrils of the user 102. Air is breathed in or inhaled at the bottom surface (as indicated by arrow 122 in FIG. 1), and passes through one or more of the channels 118, 120 (as indicated by arrow 124 in FIG. 3). The air passes through the channels 118, 120 along a substantially linear direction, although it should be understood that the air itself may be turbulent. As the air passes through the channels 118, 120, heat exchange occurs between the air and the component 108 disposed with the manipulation enclosure 106, thereby cooling the air to a predetermined temperature. The humidity of the air can also be modified as the air passes through the channels 118, 120. The modified air exists the apparatus 100 through the extensions 110, 112 (as indicated by arrow 126 of FIG. 3), and enters the air passages of the user 102 during inhalation. The user 102 thereby inhales air that has been modified by the apparatus 100. In some embodiments, the apparatus 100 can modify the odor or smell of the air during manipulation such that the air inhaled by the user 102 includes a modified and more pleasant smell for the user 102.

Figure 4:
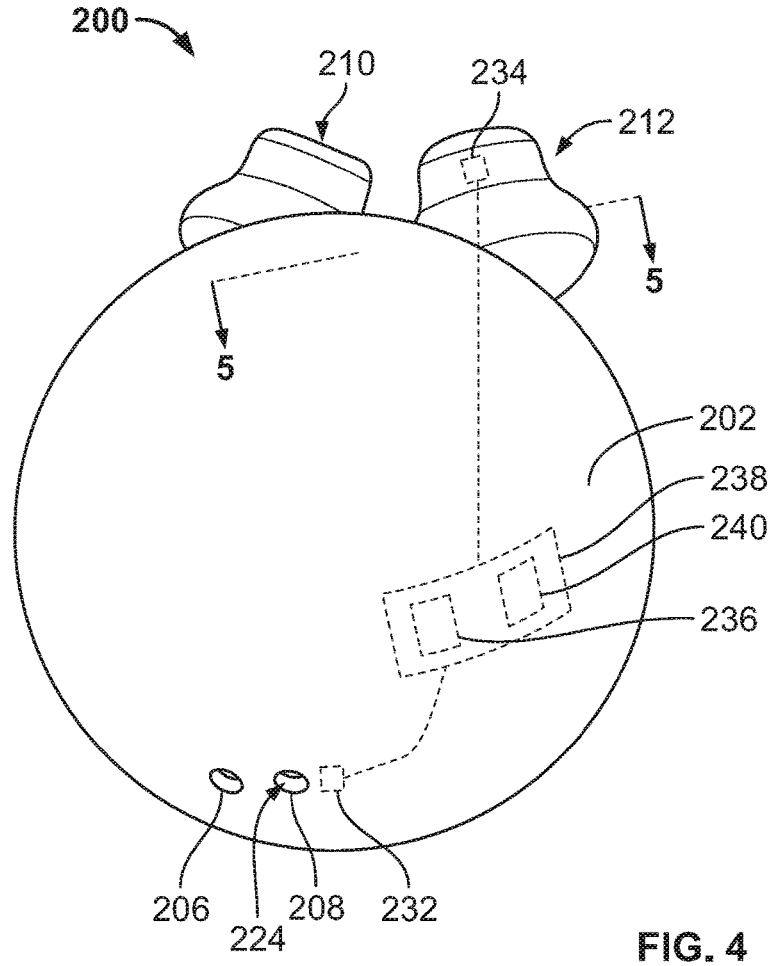
FIG. 4 is a perspective view an exemplary apparatus for manipulating characteristics of inhaled air according to the present disclosure.
Figure 5:
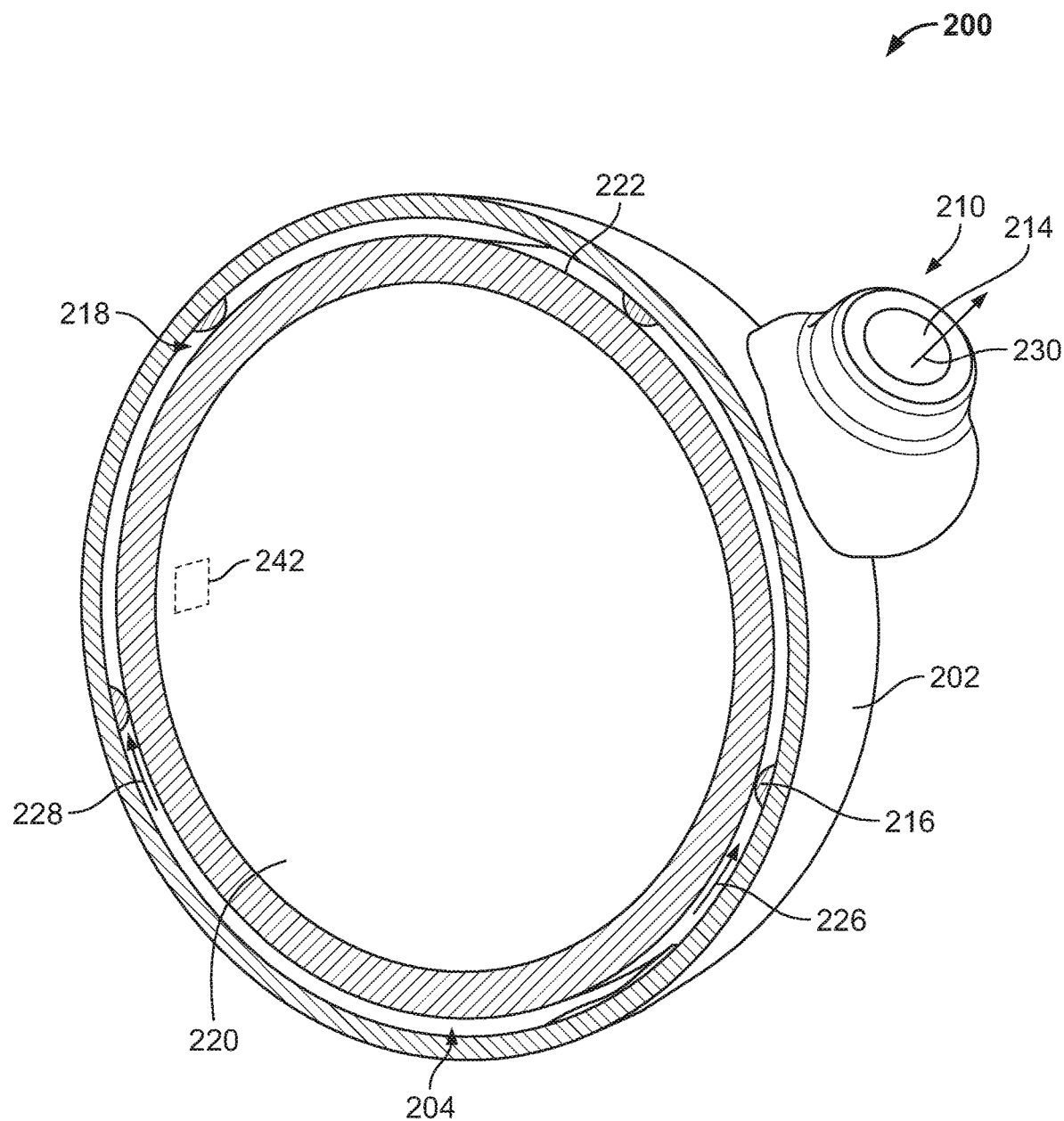
FIG. 5 is a cross-sectional view of an exemplary apparatus for manipulating characteristics of inhaled air of FIG. 4 along line 5-5.
Figure 6:
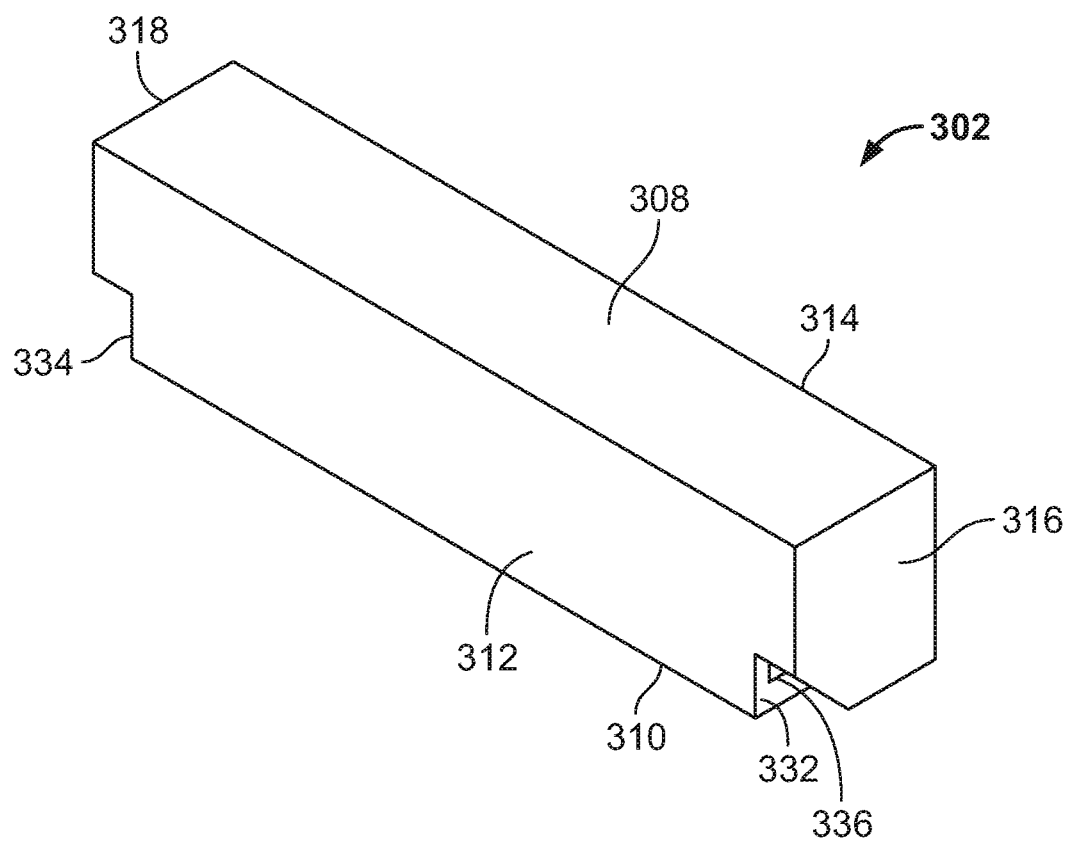
FIG. 6 is a rear perspective view of an outer housing of an exemplary apparatus for manipulating characteristics of inhaled air according to the present disclosure.
Figure 7:
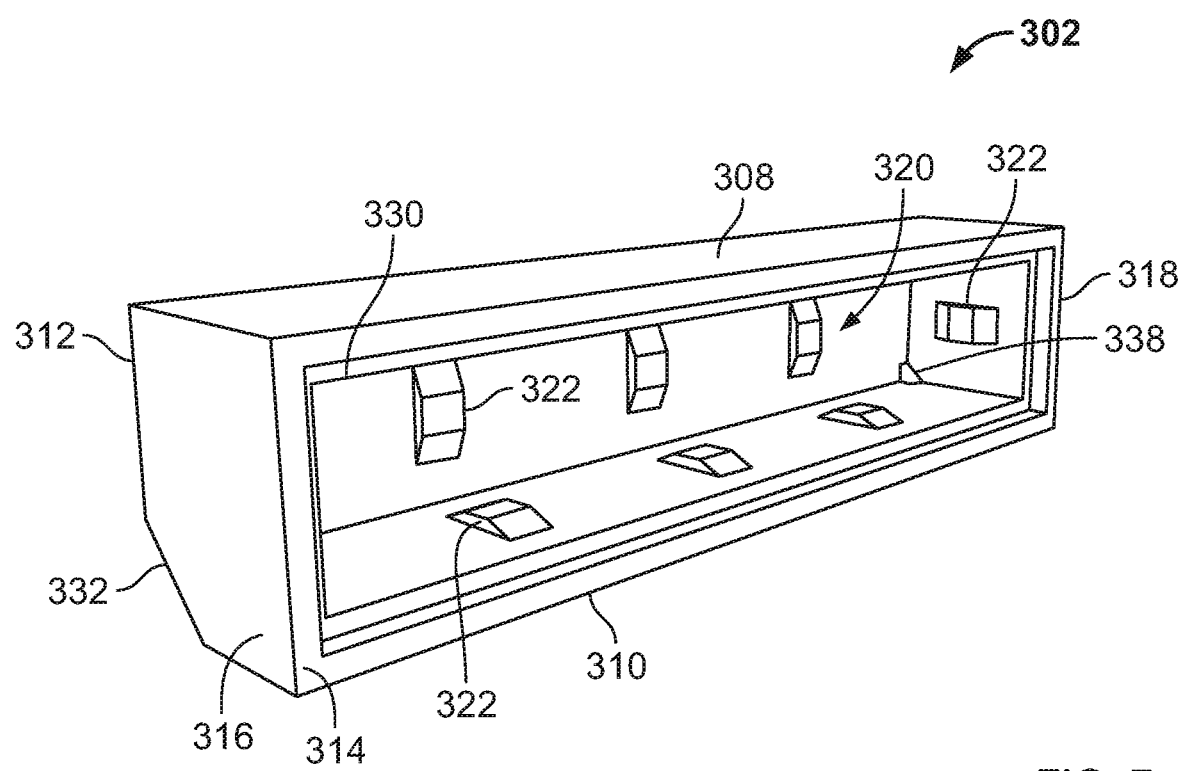
FIG. 7 is a front perspective view of an outer housing of an exemplary apparatus for manipulating characteristics of inhaled air of FIG. 6.
Figure 8:
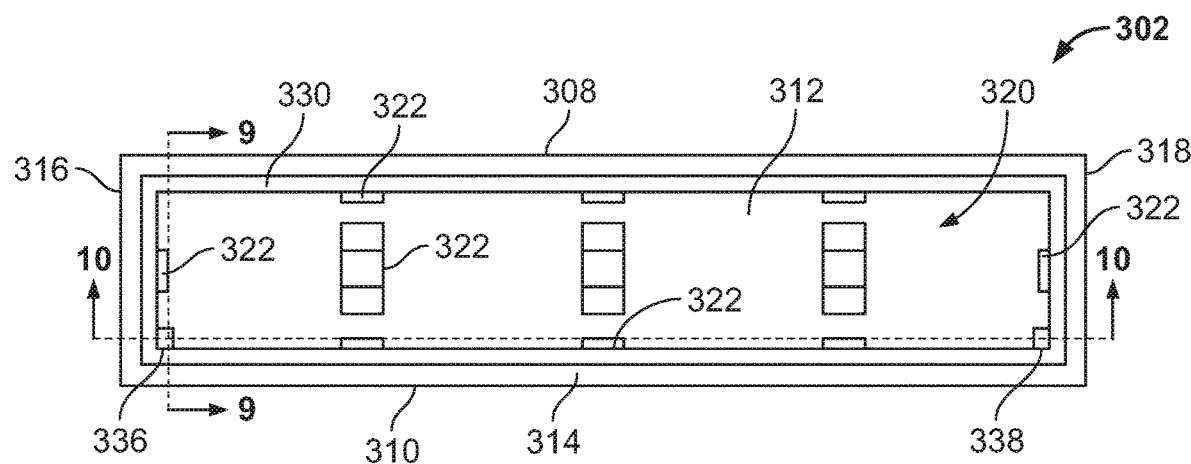
FIG. 8 is a front view of an outer housing of an exemplary apparatus for manipulating characteristics of inhaled air of FIG. 6.
Figure 9:
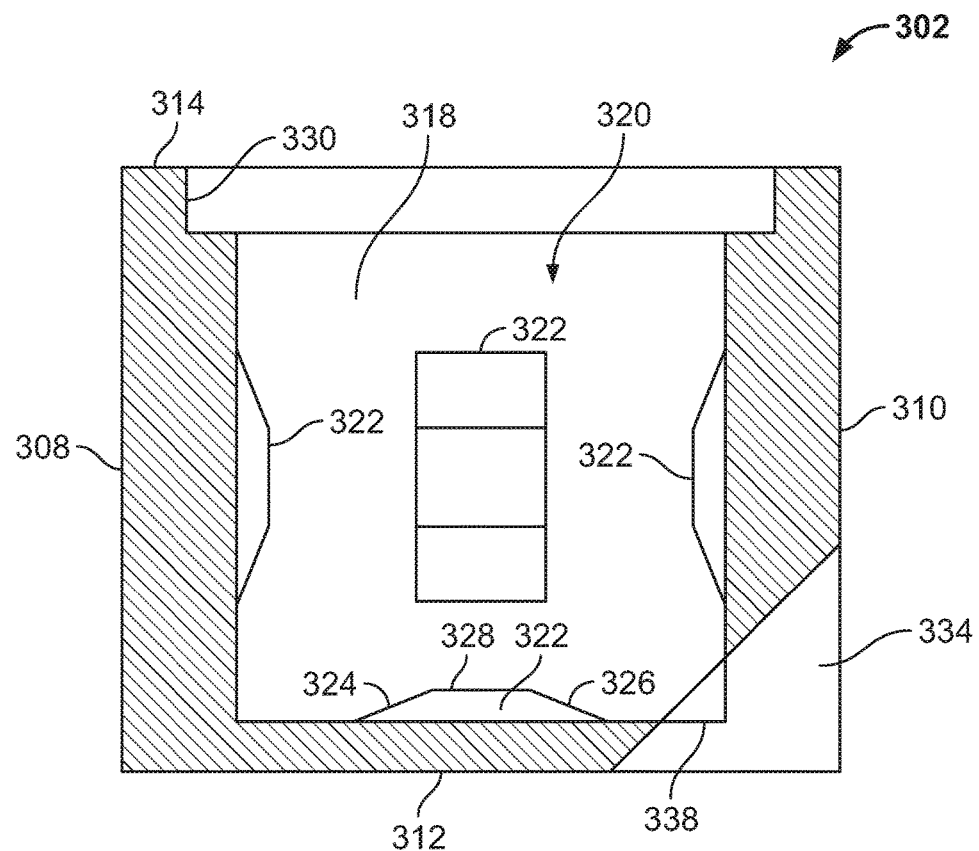
FIG. 9 is a cross-sectional view of an outer housing of an exemplary apparatus for manipulating characteristics of inhaled air of FIG. 8 along line 9-9.
Figure 10:
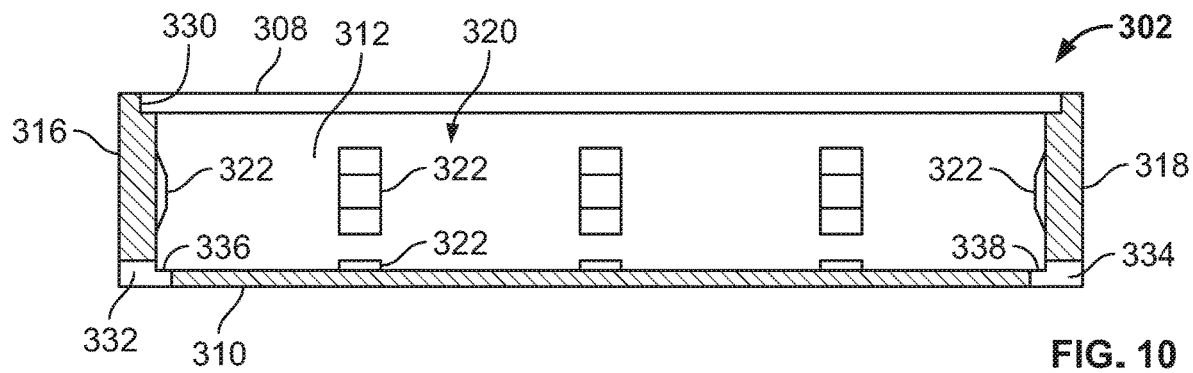
FIG. 10 is a cross-sectional view of an outer housing of an exemplary apparatus for manipulating characteristics of inhaled air of FIG. 8 along line 10-10.

FIGS. 4 and 5 show perspective and cross-sectional views of an exemplary apparatus 200 for manipulating or changing one or more characteristics of air to be inhaled by a user. The apparatus 200 can be substantially similar in structure and/or function to the apparatus 100, except for the distinctions noted here. The apparatus 200 includes a body with an outer housing 202 defining a substantially spherical shape. The outer housing 202 includes a hollow interior 204 configured to receive additional components of the apparatus 200. The outer housing 202 includes one or more holes 206, 208 extending into the hollow interior 204 from an outer surface on one side of the outer housing 202, and two extensions 210, 212 extending from the outer surface of the outer housing 202 on an opposing side of the outer housing 202. Each extension 210, 212 can define a substantially cylindrical or bulbous shape capable of confirming to the inner area of the respective nostrils of the user. The extensions 210, 212 can be fabricated from a flexible material, e.g., silicon, rubber, or the like, to better conform with the inner walls of the nostrils of the user. Each extension 210, 212 includes an inner passage 214 extending into the interior 204 of the outer housing 202. The size of the inner passage 214 can be selected based on the estimated size of the uncongested nostril of the user (as discussed above).

The inner surface of the housing 202 includes one or more support structures 216 extending from the inner surface and towards the center of the housing 202. The height of each of the support structures 216 (as measured between the uppermost point of the structure 216 and the inner surface of the housing 202) can be about, e.g., less than or equal to 1 mm, 1-2 mm, 1.1-1.9 mm, 1.2-1.8 mm, 1.3-1.7 mm, 1.4-1.6 mm, 1-1.5 mm, 1-1.4 mm, 1-1.3 mm, 1-1.2 mm, 1-1.1 mm, 1.5-2 mm, 2-10 mm, 0.2 mm, 0.5 mm, 0.7 mm, 1 mm, 1.1 mm, 1.2 mm, 1.3 mm, 1.4 mm, 1.5 mm, 1.6 mm, 1.7 mm, 1.8 mm, 1.9 mm, 2 mm, or the like. As discussed in greater detail below, the height of the support structures 216 assists in defining the width or hydraulic diameter of the channel 218 within the apparatus 200. The apparatus 200 includes a manipulation enclosure 222 disposed within the interior of the housing 202. The manipulation enclosure 222 is capable of receiving therein an air characteristic manipulation component 220 (e.g., a phase change material, a thermal storage material, a desiccant, combinations thereof, or the like). The manipulation enclosure 222 can define a shape substantially complementary to the outer housing 202, but dimensioned smaller to fit within the outer housing 202. In some embodiments, the manipulation enclosure 222 can define a hollow, spherical configuration (as shown in FIG. 5). In some embodiments, the manipulation enclosure 222 can be fabricated from a thermally conductive material, e.g., aluminum, or the like, to promote heat exchange between the air within the channel 218 and the component 220.

The support structures 216 of the outer housing 202 maintain the manipulation enclosure 222 spaced from the inner wall of the outer housing 202 to define the substantially continuous micro-channel 218 around the outer surface of the manipulation enclosure 222. In particular, the support structures 216 abut the outer surface of the manipulation enclosure 222 to maintain a predetermined distance between the outer surface of the manipulation enclosure 222 and the inner surface of the outer housing 202. As used herein, the term substantially continuous is understood to mean that the channel 218 passes around the entire outer surface of the manipulation enclosure 222, except for the minor areas in which the support structures 216 are positioned against the outer surface of the manipulation enclosure 222. In some embodiments, minor areas of contact between the support structures 216 and the manipulation enclosure 222 can be about, e.g., 0.5%-5%, 0.5-4%, 0.5-3%, 0.5-2%, 0.5-1%, 0.5%, 1%, 2%, 3%, 4%, 5%, or the like, of the entire outer surface of the manipulation enclosure 222.

The substantially continuous channel 218 provides the greatest surface area for heat exchange to occur between the air within the channel 218 and the outer surface of the manipulation enclosure 222. The design and configuration of the apparatus 200 assists in minimizing the heat exchange between the component 220 and any surface, material or fluid that is not assisting in manipulating the characteristics of air breathed in by the user. In some embodiments, the housing 202 can be fabricated from a material that is not a good conductor of heat (e.g., plastic, wood, combinations thereof, or the like) to reduce undesired manipulation of air passing through the apparatus 200.

During use, the user places the apparatus 200 in the desired location on the face of the user, and inserts one or both of the extensions 210, 212 into the respective nostril of the user. In some embodiments, if a wider nose extension is used (see, e.g., FIG. 18), the extension can be placed at least partially around a bottom portion of the nose of the user to enclose at least one nostril. As the user breathes in, air enters into the apparatus through the holes 206, 208 (as indicated by arrow 224 of FIG. 4). The holes 206, 208 are in fluid communication with the inner channel 218 such that any air that enters through the holes 206, 208 travels within the channel 218 around the manipulation enclosure 222 (as indicated by arrows 226, 228 of FIG. 5). The size of the holes 206, 208 (or the area defined by the holes 206, 208) can be selected based on the effective nostril area of the user. As the air passes around the manipulation enclosure 222 in the channel 218, a heat exchange occurs between the component 220 and the air to modify the temperature and/or humidity of the air. After the air has passed over the manipulation enclosure 222, the modified air passes through the inner passage 214 of the extensions 210, 212 (as indicated by arrow 230 of FIG. 5) and is inhaled by the user. The user thereby inhales air that has been modified by the apparatus 200.

In some embodiments, the apparatus 200 can include a feedback loop for automatically or substantially automatically controlling the characteristics of the breathed air, e.g., temperature and/or humidity. The apparatus 200 can include one or more sensors to assist in operating the feedback loop. As an example the apparatus 200 can include one or more sensors 232 disposed at, near or within the holes 206, 208 for detecting the characteristics of ambient air surrounding the apparatus 200. The apparatus 200 can include one or more sensors 234 disposed at, near or within the passages 214 of the extensions 210, 212 for detecting the characteristics of modified air to be inhaled by the user. The sensors 232, 234 can be in communication with a processing device 236 (e.g., controlling or computing mechanism) for receiving and processing the data from the sensors 232, 234. In some embodiments, the processing device 236 can be part of or associated with a user interface 238 having a graphical user interface 240 capable of receiving input from the user. In some embodiments, the apparatus 200 can include one or more sensors 242 disposed at, near or within the component 220 for detecting the temperature, humidity and/or condition of the component 220.

The data recorded by the sensors 232, 234, 242 can be transmitted to the processing device 236 for processing. The processing device 236 can be programmed to allow for manual and/or automatic control of the modification/manipulation of the characteristics of breathed air by the apparatus 200. For manual control, the user can input into the user interface 238 the desired temperature and/or humidity of the inhaled air and, based on the data from the sensors 232, 234, 242, the processing device 236 can adjust operation of the apparatus 200 to achieve the desired temperature and/or humidity input by the user. For automatic control, the processing device 236 can automatically adjust the manipulation of the air to be inhaled by the user based on the data from the sensors 232, 234, 242.

Figure 11:
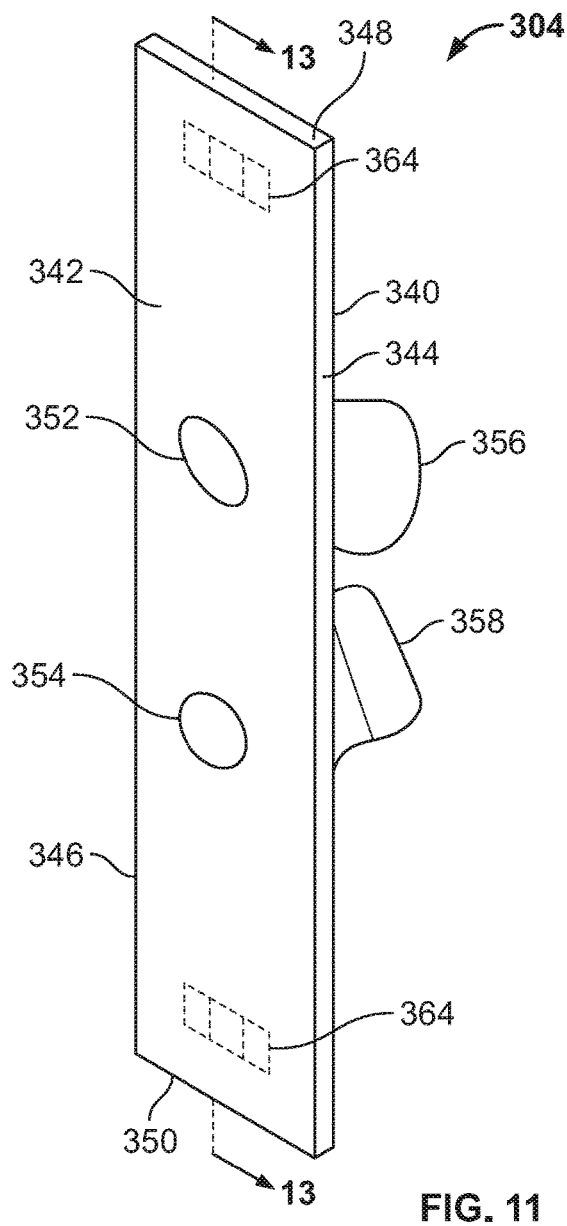
FIG. 11 is a rear perspective view of a cover of an exemplary apparatus for manipulating characteristics of inhaled air according to the present disclosure.
Figure 12:
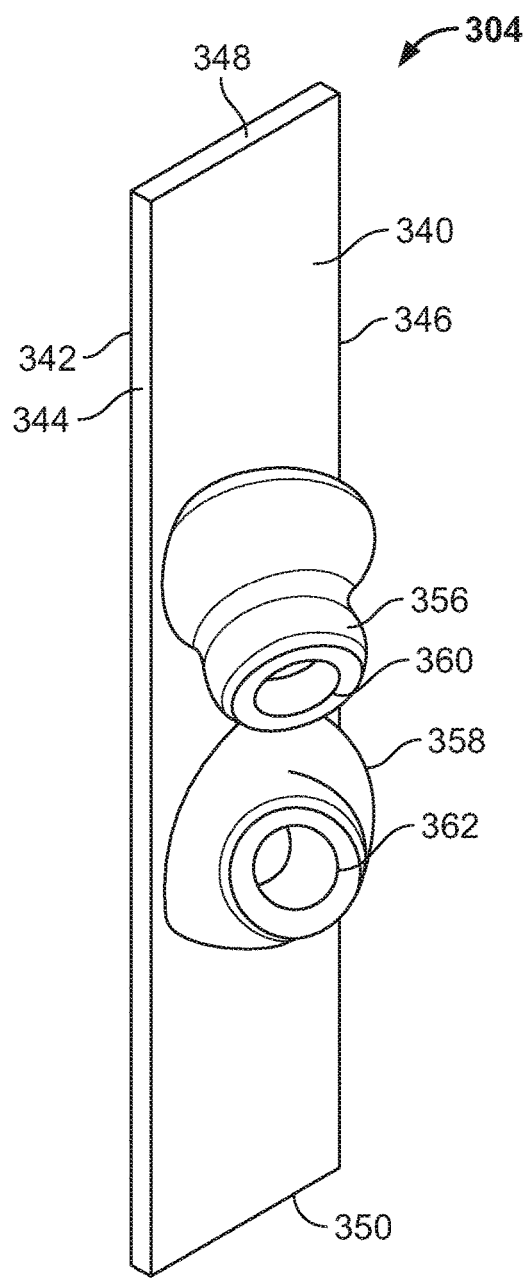
FIG. 12 is a front perspective view of a cover of an exemplary apparatus for manipulating characteristics of inhaled air of FIG. 11.
Figure 13:
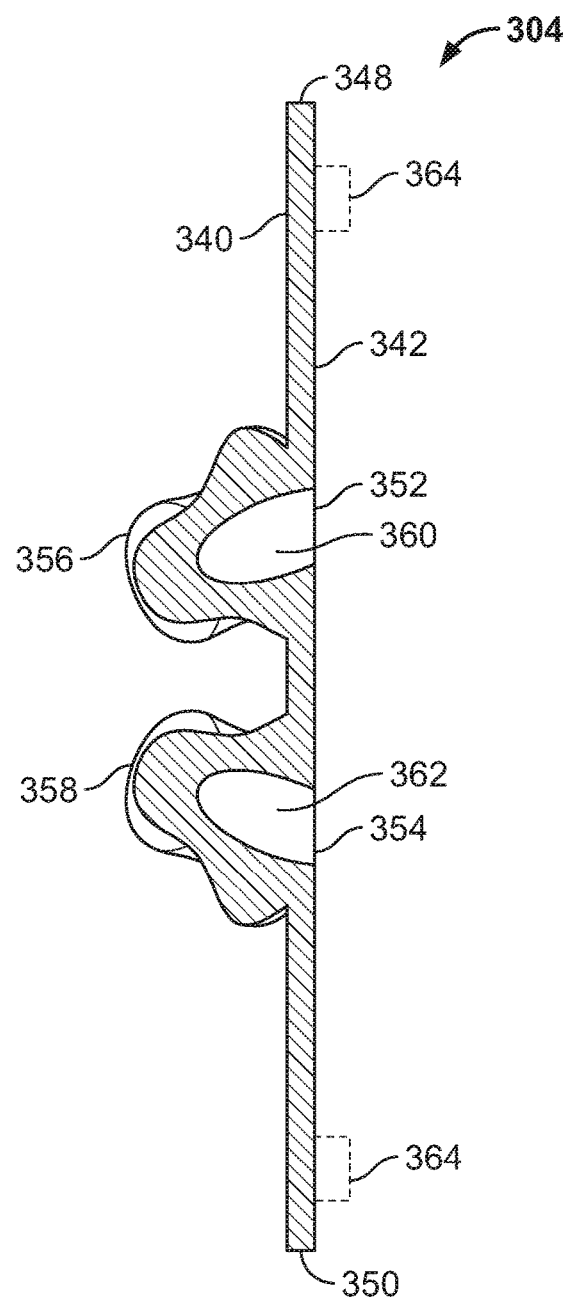
FIG. 13 is a cross-sectional view of a cover of an exemplary apparatus for manipulating characteristics of inhaled air of FIG. 11 along line 13-13.
Figure 14:
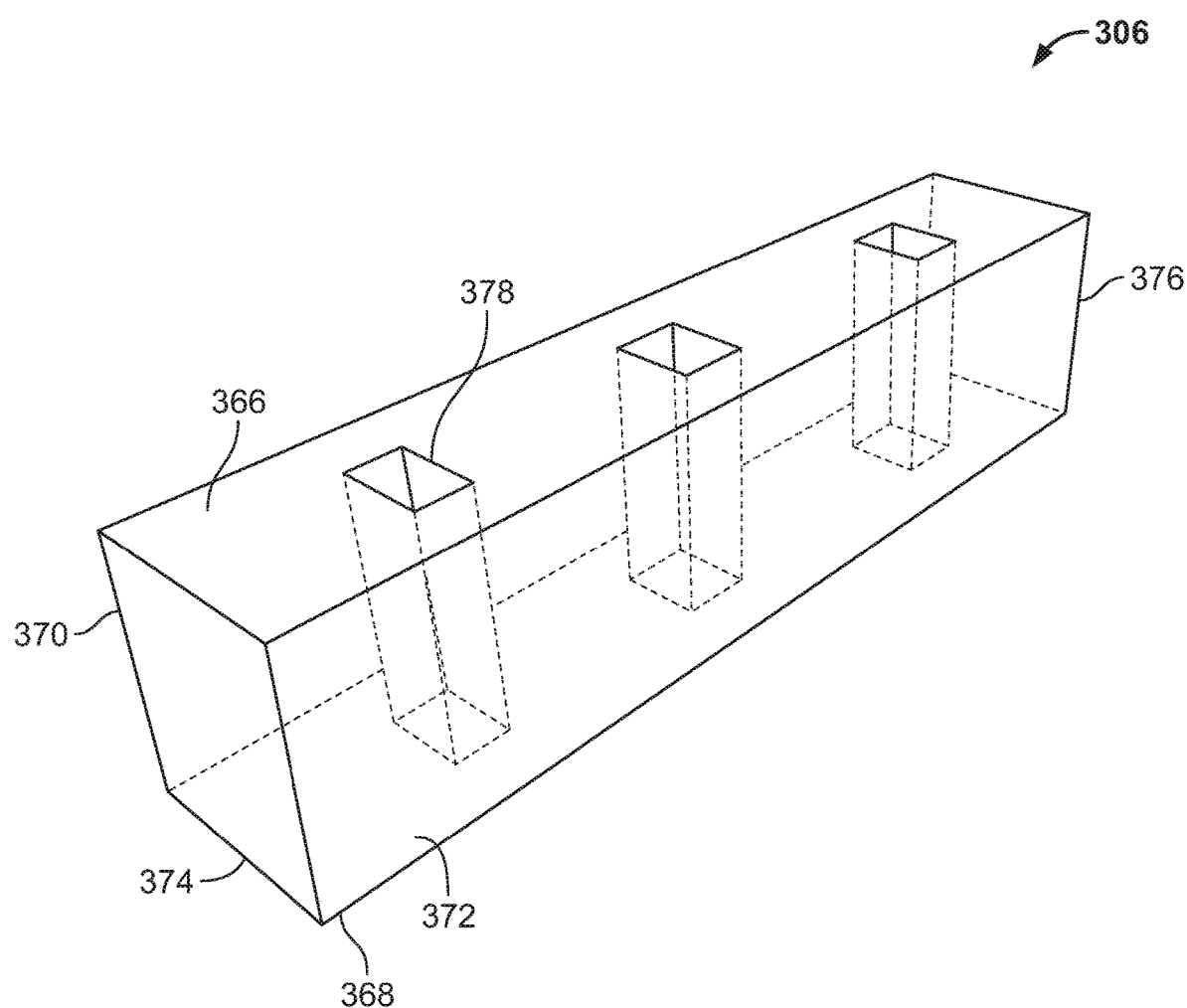
FIG. 14 is a perspective view of a manipulation enclosure of an exemplary apparatus for manipulating characteristics of inhaled air according to the present disclosure, the manipulation enclosure capable of receiving therein an air characteristic manipulation component.
Figure 15:
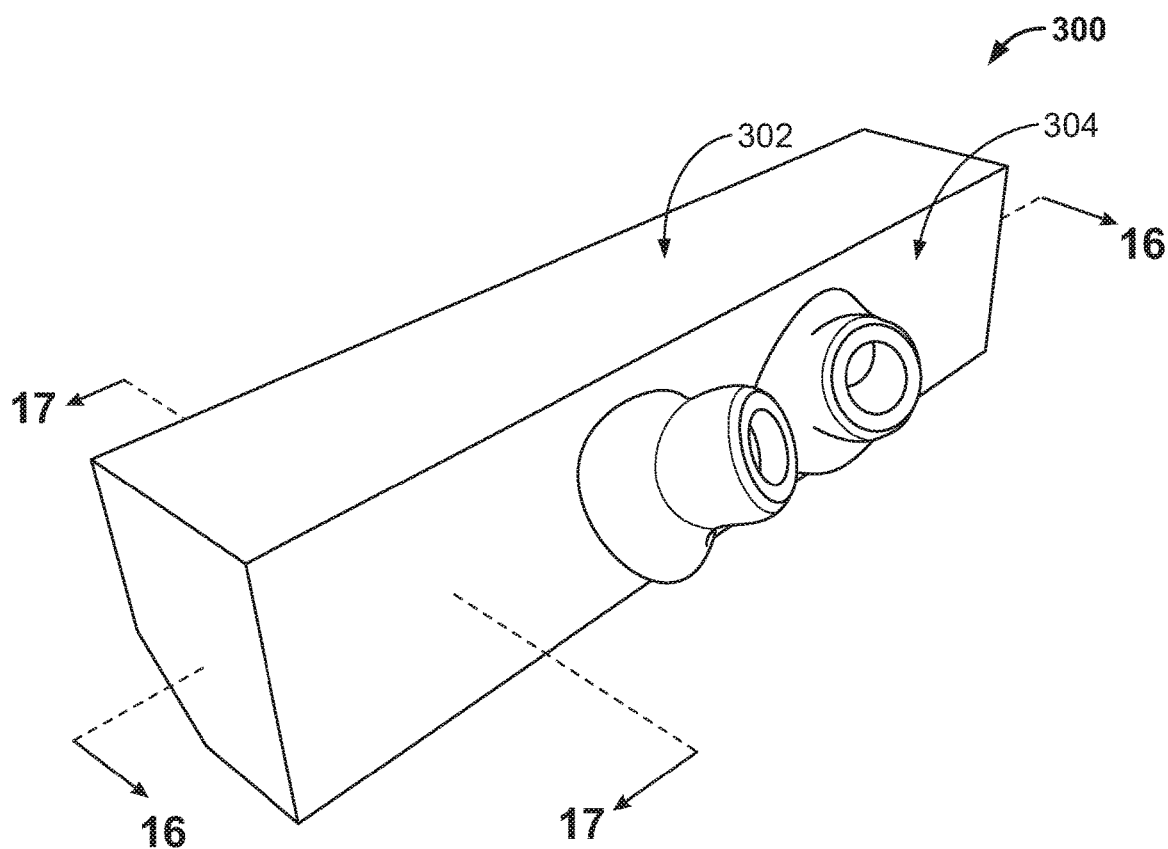
FIG. 15 is a perspective view of an exemplary apparatus for manipulating characteristics of inhaled air according to the present disclosure.
Figure 16:
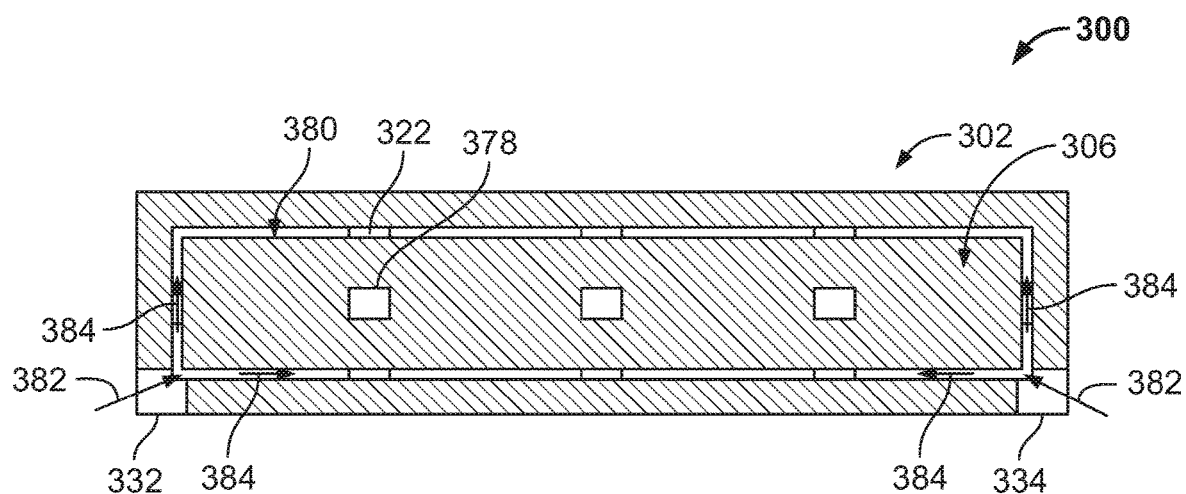
FIG. 16 is a cross-sectional view of an exemplary apparatus for manipulating characteristics of inhaled air of FIG. 15 along line 16-16.
Figure 17:
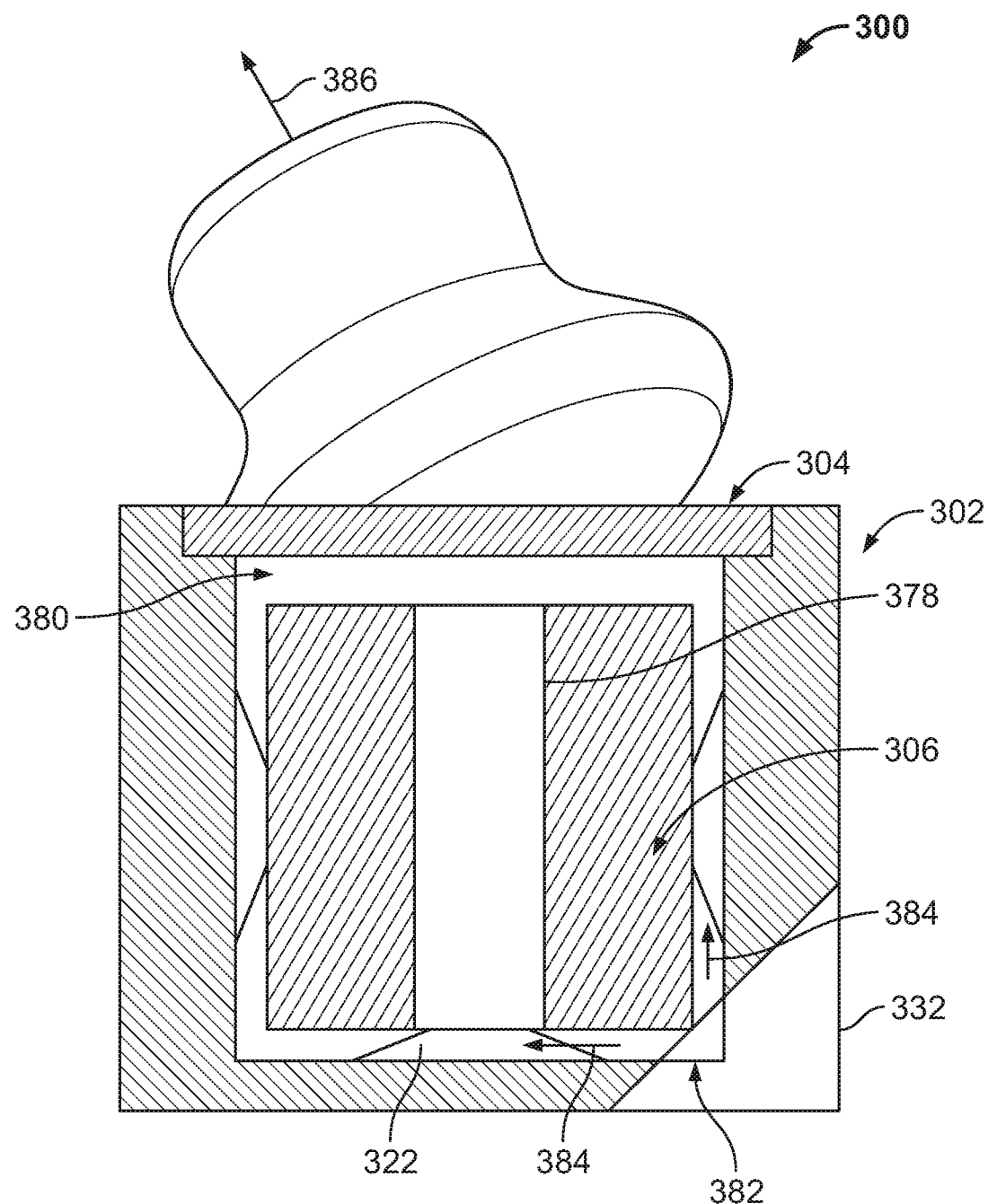
FIG. 17 is a cross-sectional view of an exemplary apparatus for manipulating characteristics of inhaled air of FIG. 15 along line 17-17.

FIGS. 6-10 are perspective, front and cross-sectional views of an outer housing 302 for an exemplary apparatus 300 for manipulating or changing one or more characteristics of air to be inhaled by a user, FIGS. 11-13 are perspective and cross-sectional views of a cover 304 of the apparatus 300, FIG. 14 is a perspective view of a manipulation enclosure 306 capable of receiving an air characteristic manipulation component for the apparatus 300, and FIGS. 15-17 are perspective and cross-sectional views of the assembled apparatus 300. With reference to FIGS. 6-10, the outer housing 302 includes a body defining a substantially rectangular configuration. Although illustrated as rectangular, it should be understood that the apparatus 300 generally can define any configuration as long as the substantially continuous heat transfer micro-channel discussed herein is maintained. The housing 302 can be fabricated from a non-thermal conducting material, e.g., plastic, polymer, wood, combinations thereof, or the like.

The outer housing 302 includes a top surface 308, an opposing bottom surface 310, a rear surface 312, a front surface 314, and side surfaces 316, 318 (e.g., walls). The top and bottom surfaces 308, 310 can be substantially parallel to each other, the front and rear surfaces 314, 312 can be substantially parallel to each other, and the side surfaces 316, 318 can be substantially parallel to each other. The outer housing 302 includes a hollow interior 320. The inner walls associated with the top, bottom, rear and side surfaces 308-312, 316, 318 can include one or more support structures 322 extending inwardly therefrom. In some embodiments, the support structures 322 can be formed on the outer surfaces of the manipulation enclosure instead of on the outer surfaces 308-312, 316, 318 of the outer housing 302. In some embodiments, the support structures 322 can be on both the inner surfaces of the outer housing 302 and the outer surfaces of the manipulation enclosure. In some embodiments, each of the support structures 322 can include tapered side walls 324, 326 extending towards an inner platform 328 extending substantially parallel to the respective inner wall of the outer housing 302 (see, e.g., FIG. 9). As will be discussed in greater detail below, the support structures 322 create a substantially continuous channel within the apparatus 300 after assembly with the manipulation enclosure 306.

In some embodiments, the front surface 314 of the outer housing 302 can include a recessed groove 330 formed therein, with the recessed groove 330 defining a step along the entire perimeter of the front surface 314. The width and length of the groove 330 are configured and dimensioned to receive the cover 304 such that the cover 304 can be assembled with the outer housing 302. The outer housing 302 and/or the cover 304 can include a rubber seal, for example, along the perimeter to ensure a substantially air tight seal between the outer housing 302 and the cover 304. The cover 304 can include a locking mechanism to maintain the cover 304 secured to the outer housing 302. Although illustrated as a recessed groove 330, it should be understood that any engagement and/or interlocking interface can be used for assembly of the cover 304 with the housing 302 (e.g., a threaded cap, a snap fit connection, a friction fit connection, combinations thereof, or the like). In some embodiments, rather than a cover 304, the apparatus 300 can include a housing 302 that completely surrounds each of the walls of the manipulation enclosure 306.

The outer housing 302 includes a chamfered or angled cutout 332, 334 on either side of the outer housing 302. Each cutout 332, 334 can extend from the rear surface 312 downward towards the bottom surface 310, with the cutout 332, 334 spaced from the top and front surfaces 308, 314. The depth of the cutouts 332, 334 (as measured by the distance from one side surface 316 to the other side surface 318) can be selected to be just sufficient enough to create an opening 336, 338 leading into the hollow interior 320 of the outer housing 302. In particular, the cutout 332, 334 creates openings 336, 338 at opposing inner corners of the hollow interior 320 such that air can enter into the hollow interior 320 from outside of the outer housing 302. The size of the opening 336, 338 can be selected to ensure that sufficient airflow is provided to the apparatus 300 and the user. In some embodiments, the size of the opening 336, 338 can be selected based on the estimated size of the uncongested nostril of the user (as discussed above).

With reference to FIGS. 11-13, the cover 304 includes a body with a substantially planar, rectangular configuration. As noted above, the configuration of the cover 304 can be selected to be substantially complementary to the recessed groove 330 formed in the outer housing 302. The cover 304 can include a front surface 340, a rear surface 342, a top surface 344, a bottom surface 346, and side surfaces 348, 350. The front and rear surfaces 340, 342 can be substantially parallel to each other, the top and bottom surfaces 344, 346 can be substantially parallel to each other, and the side surfaces 348, 350 can be substantially parallel to each other.

The cover 304 includes one or more holes 352, 354 extending from the rear surface 342 to the front surface 340. The holes 352, 354 fluidly connect with respective extensions 356, 358 protruding from the front surface 340 of the cover 304. Each of the extensions 356, 358 includes inner passages 360, 362 extending therethrough. After assembly of the apparatus 300, the holes 352, 354 are in fluid communication with the hollow interior 320 of the outer housing 302, and the holes 352, 354 are further in fluid communication with the inner passages 360, 362 to allow for inhalation of the modified air from the apparatus 300 through the extensions 356, 358. The extensions 356, 358 can be fabricated from a flexible material, e.g., silicon, rubber, or the like, to allow for at least partial insertion in the nostrils of the user. In some embodiments, the extensions 356, 358 can be fabricated from a non-flexible material, e.g., plastic, rigid rubber, or the like. In some embodiments, the rear surface 342 of the cover 304 can include two or more support structures 364 substantially similar to support structures 322 of the outer housing 302 to maintain the predetermined distance between the cover 304 and the manipulation enclosure 306 after assembly of the apparatus 300, thereby maintaining the micro-channel between the outer housing 302 and the cover 304, and the manipulation enclosure 306.

With reference to FIG. 14, the manipulation enclosure 306 for receiving an air characteristic manipulation component is provided. The manipulation enclosure 306 can define a substantially rectangular configuration complementary to the hollow interior 320 of the outer housing 302. The manipulation enclosure 306 can include a front surface 366, a rear surface 368, a top surface 370, a bottom surface 372, and side surfaces 374, 376. The front and rear surfaces 366, 368 can be substantially parallel to each other, the top and bottom surfaces 370, 372 can be substantially parallel to each other, and the side surfaces 374, 376 can be substantially parallel to each other. The manipulation enclosure 306 can define a substantially hollow interior that can be filled with or contains an air characteristic manipulation component, e.g., a thermal storage material, a phase change material, a desiccant, water, any phase change material with a melting temperature of less than 20° C., combinations thereof, or the like.

In some embodiments, the manipulation enclosure 306 can include one or more passages 378 extending therethrough. For example, as shown in FIG. 14, the manipulation enclosure 306 can include three passages 378 extending through the body of the manipulation enclosure 306 between the front and rear surfaces 366, 368. Each of the passages 378 can define a substantially uniform cross-section. In some embodiments, the cross-section of the passages 378 can be non-uniform. The passages 378 provide for additional air flow around the manipulation enclosure 306 to improve the efficiency of heat transfer during use of the apparatus 300. Although illustrated as rectangular in configuration, it should be understood that the passages 378 can be any type of shape and/or configuration.

The manipulation enclosure 306 can be removed from the apparatus 300. For example, if the air characteristic manipulation component is to be recharged, in some embodiments, the entire apparatus 300 can be placed in the freezer. In some embodiments, the manipulation enclosure 306 can be removed from the apparatus 300 and placed in the freezer on its own. The manipulation enclosure 306 can be interchangeable with other manipulation enclosures 306. For example, while one manipulation enclosure 306 is recharging, another manipulation enclosure 306 having the same configuration can be placed within the apparatus 300. It should be understood that the manipulation enclosures of the apparatus 100, 200, 400 discussed herein can be similarly removed from the respective apparatus 100, 200, 400.

With reference to FIGS. 15-17, perspective and cross-sectional views of the assembled apparatus 300 are provided. During assembly, the manipulation enclosure 306 can be inserted into the hollow interior 320 of the outer housing 302. The support structures 322 abut the outer surfaces of the manipulation enclosure 306 to create a micro-channel 380 between each of the outer surfaces of the manipulation enclosure 306 and the inner surfaces of the outer housing 302. In some embodiments, the micro-channel 380 can be formed only around some of the outer surfaces of the manipulation enclosure 306. Next, the cover 304 can be positioned into the recessed groove 330 in the outer housing 302. The support structures 364 of the cover 304 can abut the outer surface of the manipulation enclosure 306 to create a micro-channel 380 between the manipulation enclosure 306 and the cover 302. The step formed by the recessed groove 330 can also assist in maintaining the distance of the cover 302 relative to the component 306. The width or hydraulic diameter of the channel or micro-channel 380 as measured between the cover 304 and outer housing 302, and the manipulation enclosure 306 can be about, e.g., less than or equal to 1 mm, 1-10 mm, 1-2 mm, 1.1-1.9 mm, 1.2-1.8 mm, 1.3-1.7 mm, 1.4-1.6 mm, 1-1.5 mm, 1-1.4 mm, 1-1.3 mm, 1-1.2 mm, 1-1.1 mm, 1.5-2 mm, 1 mm, 1.1 mm, 1.2 mm, 1.3 mm, 1.4 mm, 1.5 mm, 1.6 mm, 1.7 mm, 1.8 mm, 1.9 mm, 2 mm, or the like. The channel or micro-channel 380 creates a substantially continuous gap around the entire manipulation enclosure 306 for heat exchange.

During use, the user can position the apparatus 300 in the desired position, e.g., between the upper lip and nose of the user. The extensions 356, 358 can be at least partially inserted into one or both the nostrils of the user to maintain the position of the apparatus 300 relative to the user. In some embodiments, a wider nose extension can be used and positioned at least partially around the bottom of the nose of the user (see, e.g., FIG. 18). As the user inhales, air can travel into the apparatus 300 through the openings 336, 338 of the outer housing 302 and into the micro-channel 380 (as indicated by arrow 382 of FIGS. 16 and 17). The air can travel within the micro-channel 380 around the manipulation enclosure 306 to modify the temperature and/or humidity of the air (as indicated by arrow 384 of FIGS. 16 and 17). In some embodiments, the air can travel through the passages 378 in the manipulation enclosure 306. The size and/or length of the micro-channel 380 and the passages 378 can be selected such that the air flow within the apparatus 300 remains substantially turbulent to enhance the heat transfer effect. The air can subsequently travel into, through and out of the extensions 356, 358, and into the nostrils of the user (as indicated by arrow 386 of FIG. 17). The characteristics of the air inhaled by the user can thereby be modified by the apparatus 300 prior to inhalation to provide comfort to the user.

Figure 18:
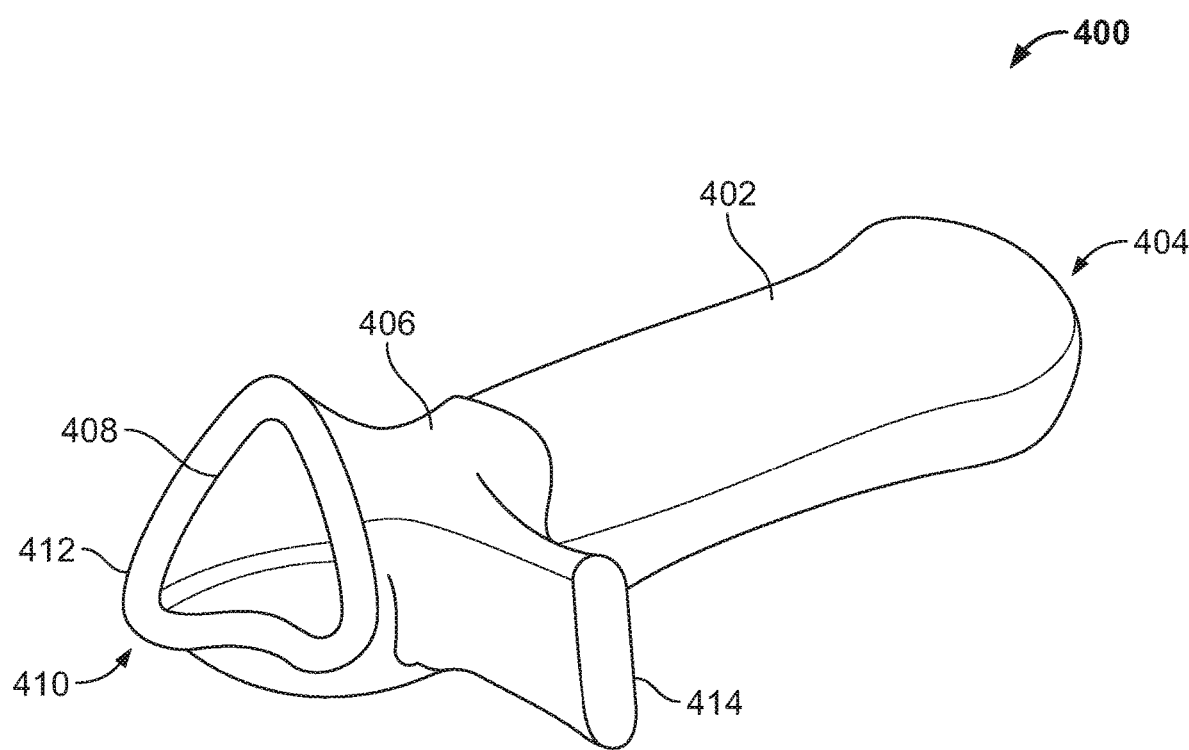
FIG. 18 is a perspective view of an exemplary apparatus for manipulating characteristics of inhaled air according to the present disclosure.

FIG. 18 shows a perspective view of an exemplary apparatus 400 for manipulating or changing one or more characteristics of air to be inhaled by a user. The apparatus 400 can be substantially similar in structure and/or function to the apparatus 100, 200, 300, except for the distinctions noted here. The apparatus 400 includes an outer housing 402 including therein a removable manipulation enclosure capable of receiving an air characteristic manipulation component (not shown). The structure of the manipulation enclosure and the inner surfaces of the outer housing 402 can form the micro-channel for passage of air around the manipulation enclosure. The distal end 404 of the outer housing 402 can include one or more openings for passage of air into the apparatus 400 as the user inhales air. The air introduced into the apparatus 400 from the distal end 404 can pass through the micro-channel around the manipulation enclosure, with the manipulation enclosure changing the humidity and/or temperature of the air prior to inhalation by the user.

Rather than including two extensions for at least partial insertion into the respective nostrils of the user, the apparatus 400 includes a single extension 406 detachably coupled to the proximal end of the outer housing 402. The extension 406 can act as a cover for the outer housing 402. The extension 406 can be fabricated from a flexible material, e.g., silicone, rubber, or the like. The extension 406 includes a wide opening 408 at the proximal end 410 of the apparatus 400. In some embodiments, the opening 408 can include a flange or lip 412 extending along the entire perimeter of the opening 408. The flange or lip 412 can define a substantially circular cross-section. In some embodiments, the opening 408 can define a substantially triangular configuration.

The opening 408 can be dimensioned to at least partially fit over the bottom portion of a nose of a user, thereby covering both nostrils of the user and the surrounding bottom area of the nose. Thus, rather than fitting individual extensions into each respective nostril, a single extension with a wide opening can be used to provide a more comfortable use of the apparatus 400. The flange or lip 412 can assist in flexing and conforming to the shape of the user's nose. In some embodiments, the flange or lip 412 can assist in maintaining the apparatus 400 detachably secured to the nose of the user. In some embodiments, the opening 408 can be dimensioned to at least partially fit over the bottom portion of one nostril of the user.

The opening 408 extends into the apparatus 400 and fluidly connects with the micro-channel within the outer housing 402 such that modified air can be inhaled through the opening 408. In some embodiments, the apparatus 400 can include one or more protrusions 414 extending from the extension 406 and/or the outer housing 402. The protrusions 414 can be used as handles by the user, providing a gripping surface to assist in positioning and maintaining the position of the apparatus 400 relative to the nose of the user.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. An apparatus for manipulating one or more characteristics of air to be inhaled, comprising:
   an outer housing including an outer surface, inner surfaces, a hollow interior, and at least one opening formed in the outer housing and extending between the outer surface and the hollow interior;
   a manipulation enclosure disposed within the hollow interior of the outer housing, the manipulation enclosure including outer surfaces, and the manipulation enclosure capable of receiving therein an air characteristic manipulation component; and
   support structures extending inwardly from the inner surfaces of the outer housing into the hollow interior and configured to abut the outer surfaces of the manipulation enclosure to form a continuous micro-channel between the outer surfaces of the manipulation enclosure and the inner surfaces of the outer housing;
   wherein the continuous micro-channel defines a width or hydraulic diameter as measured between the inner surfaces of the outer housing and the outer surfaces of the manipulation enclosure of less than or equal to about 1.0 mm; and
   wherein the width or hydraulic diameter of the continuous micro-channel is uniform around the outer surfaces of the manipulation enclosure.

2. The apparatus of claim 1, comprising a cover detachable from the outer housing, wherein the continuous micro-channel is formed between the manipulation enclosure and the cover.

3. The apparatus of claim 2, wherein the cover includes one or more additional support structures extending inwardly into the hollow interior of the outer housing from an inner surface of the cover, wherein the one or more additional support structures of the cover abut at least one of the outer surfaces of the manipulation enclosure to form the continuous micro-channel around the manipulation enclosure.

4. The apparatus of claim 1, wherein the continuous micro-channel extends entirely around each of the outer surfaces of the manipulation enclosure.

5. The apparatus of claim 2, wherein a front surface of the outer housing includes a recessed groove configured and dimensioned to at least partially received the cover therein.

6. The apparatus of claim 1, comprising at least one extension protruding from one surface of the apparatus, and at least one hole extending through the apparatus to fluidly connect the at least one extension with the continuous micro-channel, the at least one extension configured to be inserted into a nostril of a user.

7. The apparatus of claim 1, comprising an extension protruding from one end of the apparatus, the extension including an opening fluidly connected to the continuous micro-channel, and the opening configured to be placed at least partially around a bottom surface of a nose of a user to cover at least one nostril of the user with the extension.

8. The apparatus of claim 1, wherein the outer housing is configured to receive the air through the at least one opening and into the continuous micro-channel, and the air characteristic manipulation component disposed within the manipulation enclosure is configured to modify at least one of a temperature or a humidity of the air prior to inhalation of modified air by a user.

9. The apparatus of claim 1, wherein the outer housing is fabricated from a flexible material that allows the outer housing to at least partially conform to a contoured area of a user's face.

10. The apparatus of claim 1, wherein the air characteristic manipulation component is at least one of a thermal storage material, a phase change material, a desiccant, or water.

11. The apparatus of claim 1, wherein the manipulation enclosure includes one or more passages formed therein, each of the one or more passages configured to allow the air passage therethrough.

12. The apparatus of claim 1, comprising a feedback loop including at least one sensor configured to detect an ambient air temperature and at least one sensor configured to detect a modified air temperature, and including a processing device configured to control manipulation of one or more characteristics of ambient air based on input from the one or more sensors of the ambient air temperature and the modified air temperature.

13. The apparatus of claim 1, wherein the at least one opening formed in the outer housing includes a first opening and a second opening, and wherein the outer housing includes a chamfered or angled cutout on either side of the outer housing at the outer surface, a depth of each chamfered or angled cutout selected to create the respective first opening and second opening.

14. The apparatus of claim 13, wherein the first opening and the second opening extend from the outer surface of the outer housing into the continuous micro-channel formed between the outer housing and the manipulation enclosure.

15. The apparatus of claim 1, wherein the continuous micro-channel facilitates heat exchange between the air passing through the continuous micro-channel and the manipulation enclosure to modify at least one characteristic of the air.

16. An apparatus for manipulating air to be inhaled, comprising:
   an outer housing including an outer surface, inner surfaces, a hollow interior, and at least one opening formed in the outer housing and extending between the outer surface and the hollow interior;
   a manipulation enclosure disposed within the hollow interior of the outer housing, the manipulation enclosure including outer surfaces, and the manipulation enclosure including an air characteristic manipulation component disposed therein; and
   a cover attached to the outer housing, the cover including an inner surface, and the cover enclosing the manipulation enclosure within the hollow interior of the outer housing; and support structures extending inwardly from the inner surfaces of the outer housing into the hollow interior and from the inner surface of the cover, the support structures configured to abut the outer surfaces of the manipulation enclosure to form a continuous-micro-channel between the outer surfaces of the manipulation enclosure, the inner surfaces of the outer housing, and the inner surface of the cover;

wherein the outer housing is configured to receive the air through the at least one opening and into the continuous micro-channel, and the air characteristic manipulation component is configured to modify at least one of a temperature or a humidity of the air prior to inhalation of modified air by a user;

wherein the continuous micro-channel defines a width or hydraulic diameter as measured between the inner surfaces of the outer housing and the outer surfaces of the manipulation enclosure, and between the inner surface of the cover and the outer surfaces of the manipulation enclosure, of less than or equal to about 1.0 mm; and wherein the width or hydraulic diameter of the continuous micro-channel is uniform around the outer surfaces of the manipulation enclosure.

17. The apparatus of claim 16, wherein the continuous micro-channel extends entirely around the outer surfaces of the manipulation enclosure.

18. A method of manipulating air to be inhaled, comprising:

introducing the air into an outer housing of an apparatus through at least one opening formed in the outer housing and extending between an outer surface of the outer housing and a hollow interior of the outer housing, the apparatus including (i) the outer housing including inner surfaces, (ii) a manipulation enclosure disposed within the hollow interior of the outer housing, the manipulation enclosure including outer surfaces, and the manipulation enclosure capable of receiving therein an air characteristic manipulation component, and (iii) support structures extending inwardly from the inner surfaces of the outer housing into the hollow interior and abutting the outer surfaces of the manipulation enclosure to form a continuous micro-channel between the outer surfaces of the manipulation enclosure and the inner surfaces of the outer housing;

passing the air around at least a portion of the manipulation enclosure to modify at least one characteristic of the air, the; and passing modified air out of the apparatus for inhalation by a user;

wherein the continuous micro-channel defines a width or hydraulic diameter as measured between the inner surfaces of the outer housing and the outer surfaces of the manipulation enclosure of less than or equal to about 1.0 mm; and wherein the width or hydraulic diameter of the continuous micro-channel is uniform around the outer surfaces of the manipulation enclosure.

\* \* \* \* \*